(12) United States Patent
Hansen et al.

(10) Patent No.: US 6,962,702 B2
(45) Date of Patent: Nov. 8, 2005

(54) PRODUCTION AND USE OF NOVEL PEPTIDE-BASED AGENTS FOR USE WITH BI-SPECIFIC ANTIBODIES

(75) Inventors: Hans J. Hansen, Slidell, LA (US); Gary L. Griffiths, Morristown, NJ (US); Shui-on Leung, Shatin (HK); William J. McBride, Summit, NJ (US); Zhengxing Qu, Warren, NJ (US)

(73) Assignee: Immunomedics Inc., Morris Plains, NJ (US)

( * ) Notice: Subject to any disclaimer, the term of this patent is extended or adjusted under 35 U.S.C. 154(b) by 179 days.

(21) Appl. No.: 09/823,746

(22) Filed: Apr. 3, 2001

(65) Prior Publication Data

US 2002/0006379 A1 Jan. 17, 2002

Related U.S. Application Data

(63) Continuation-in-part of application No. 09/337,756, filed on Jun. 22, 1999
(60) Provisional application No. 60/104,156, filed on Oct. 14, 1998, and provisional application No. 60/090,142, filed on Jun. 22, 1998.

(51) Int. Cl.$^7$ ............................................. A61K 39/395
(52) U.S. Cl. .................. 424/136.1; 424/1.53; 424/9.34; 424/94.61; 424/133.1; 424/155.1; 424/156.1; 424/179.1; 424/181.1; 424/183.1
(58) Field of Search ................................. 424/1.53, 9.34, 424/94.61, 133.1, 136.1, 179.1, 181.1, 183.1, 155.1, 156.1

(56) References Cited

U.S. PATENT DOCUMENTS

| | | | | |
|---|---|---|---|---|
| 4,818,709 A | * | 4/1989 | Primus et al. | 436/518 |
| 5,274,076 A | * | 12/1993 | Barbet et al. | 530/330 |
| 5,683,694 A | * | 11/1997 | Bagshawe et al. | 424/178.1 |
| 6,096,289 A | * | 8/2000 | Goldenberg | 424/1.49 |

FOREIGN PATENT DOCUMENTS

WO 9966951 * 12/1999

* cited by examiner

Primary Examiner—David Saunders
(74) Attorney, Agent, or Firm—Heller Ehrman LLP

(57) ABSTRACT

The present invention relates to a bi-specific antibody or antibody fragment having at least one arm that is reactive against a targeted tissue and at least one other arm that is reactive against a linker moiety. The linker moiety encompasses a hapten to which antibodies have been prepared. The antigenic linker is conjugated to one or more therapeutic or diagnostic agents or enzymes. The invention provides constructs and methods for producing the bispecific antibodies or antibody fragments, as well as methods for using them.

30 Claims, 7 Drawing Sheets

GACATTGTGATGTCACAATCTCCATCCTCCCTGGCTGTGTCACCAGGAGAGAAGGTCACTATGACCTGCAAATCCAGTCAGAGTCTGTTC    90
 D   I   V   M   S   Q   S   P   S   S   L   A   V   S   P   G   E   K   V   T   M   T   C   K   S   S   Q   S   L   F    30

AACAGTAGAACCCGAAAGAACTACTTGGGTTGGTACCAGCAGAAACCAGGGCAGTCTCCTAAACTTCTGATCTACTGGGCATCTACTCGG   180
 N   S   R   T   R   K   N   Y   L   G   W   Y   Q   Q   K   P   G   Q   S   P   K   L   L   I   Y   W   A   S   T   R    60
 ────────CDR1────────                                                                        ─────CDR2─────

GAATCTGGGGTCCCTGATCGCTTCACAGGCAGTGGATCTGGGACAGATTCACTCTCACCATCAACAGTGTGCAGTCTGAAGACCTGGCA    270
 E   S   G   V   P   D   R   F   T   G   S   G   S   G   T   D   F   T   L   T   I   N   S   V   Q   S   E   D   L   A    90

GTTTATTACTGCACTCAAGTTTATTATCTGTGCACGTTCGGTGCTGGGACCAAGCTGGAGCTGAAACGG    339
 V   Y   Y   C   T   Q   V   Y   Y   L   C   T   F   G   A   G   T   K   L   E   L   K   R    113
             ──────────CDR3──────────

Figure 1.

```
GTCCAACTGCAGGAGTCAGGGGGAGACTTAGTGAAGCCTGGAGGGTCCCTGAAACTCTCCTGTGCAGCCTCTGGATTCACTTTCAGTATT        90
 V  Q  L  Q  E  S  G  G  D  L  V  K  P  G  G  S  L  K  L  S  C  A  A  S  G  F  T  F  S  I         30

TACACCATGTCTTGGCTTCGCCAGACTCCGGAAAAGAGGCTGGAGTGGGTCGCAACCCTGAGTGGTGATGGTGATGACATCTACTATCCA       180
 Y  T  M  S  W  L  R  Q  T  P  E  K  R  L  E  W  V  A  T  L  S  G  D  G  D  D  I  Y  Y  P         60
    CDR1                                                     CDR2

GACAGTGTGAAGGGTCGATTCACCATCTCCAGAGACAACGCCAAGAACAACCTATATCTGCAAATGAACAGTCTAAGGTCTGCGGACACG       270
 D  S  V  K  G  R  F  T  I  S  R  D  N  A  K  N  N  L  Y  L  Q  M  N  S  L  R  S  A  D  T         90

GCCTTGTATTACTGTGCAAGGGTGCGACTTGGGGACTTCGATGTCTGGGGCCCAGGGACCACGGTCTCCGTCTCCTCA                   354
 A  L  Y  Y  C  A  R  V  R  L  G  D  W  D  F  D  V  W  G  P  G  T  T  V  S  V  S  S              118
                    CDR3
```

Figure 2.

```
GACATTGTGATGTCACAATCTCCATCCTCCCTGGCTGTGTCACCAGGAGAGAAGGTCACTATGACCTGCAAATCCAGTCAGAGTCTGTTC      90
 D  I  V  M  S  Q  S  P  S  S  L  A  V  S  P  G  E  K  V  T  M  T  C  K  S  S  Q  S  L  F      30
                                                                        Vk CDR1

AACAGTAGAACCCGAAAGAACTACTTGGGTTGGTACCAGCAGAAACCAGGGCAGTCTCCTAAACTTCTGATCTACTGGGCATCTACTCGG     180
 N  S  R  T  R  K  N  Y  L  G  W  Y  Q  Q  K  P  G  Q  S  P  K  L  L  I  Y  W  A  S  T  R       60
 Vk CDR1                                                                    Vk CDR2

GAATCTGGGGTCCCTGATCGCTTCACAGGCAGTGGATCTGGGACAGATTTCACTCTCACCATCAACAGTGTGCAGTCTGAAGACCTGGCA     270
 E  S  G  V  P  D  R  F  T  G  S  G  S  G  T  D  F  T  L  T  I  N  S  V  Q  S  E  D  L  A       90

GTTTATTACTGCACTCAAGTTTATTATCTGTGCACGTTCTTTGGAGCTGGGACCAAGCTGGAGCTGAAACGAGGAGGTGGCGGATCAGGAGGC    360
 V  Y  Y  C  T  Q  V  Y  Y  L  C  T  F  G  A  G  T  K  L  E  L  K  R  G  G  G  G  S  G  G      120
            Vk CDR3                                                         Linker GGAGGCTCCGAGGCCGTGGGAGCTGAGGTGCAGCTGGAGGAGTCTGGGGGAGACTTAGTGAAGCCTGGAGGGTCCCTGAAACTCTCCTGT     450
 G  G  G  G  S  E  V  Q  L  E  E  S  G  G  D  L  V  K  P  G  G  S  L  K  L  S  C                150
 Linker GCAGCCTCTGGATTCACTTTCAGTATTTACACCATGTCTTGGCTTCGCCAGACTCCGGAAAAGAGGCTGGAGTGGGTCGCAACCCTGAGT     540
 A  A  S  G  F  T  F  S  I  Y  T  M  S  W  L  R  Q  T  P  E  K  R  L  E  W  V  A  T  L  S      180
                         VH CDR1

GGTGATGGTGATGACAATACTACTACCAGACAGTGTGAAGGGTCGATTCACCATCTCCAGAGACAATGCCAAGAACAACCTATATCTGCAA     630
 G  D  G  D  D  I  Y  Y  P  D  S  V  K  G  R  F  T  I  S  R  D  N  A  K  N  N  L  Y  L  Q      210
          VH CDR2

ATGAACAGTCTAAGGTCTGCGGACACGGCCCTTGTATTACTGTGCAAGGGTGCGACTTGGGGACTTGGACTTCGATGTCTGGGGCCAAGGG     720
 M  N  S  L  R  S  A  D  T  A  L  Y  Y  C  A  R  V  R  L  G  D  W  D  F  D  V  W  G  Q  G      240
                                        VH CDR3

ACCACGGGTCACCGTCTCCTCA                                                                         741
 T  T  V  T  V  S  S                                                                           247
```

Figure 3.

```
GCTGTTTTGATGACCCAAACTCCACTCTCCCTGCCTGTCAGTCTTGGAGATCAAGCCTCCATCTCTTGCAGATCTAGTCAGAGCATTGTC    90
 A  V  L  M  T  Q  T  P  L  S  L  P  V  S  L  G  D  Q  A  S  I  S  C  R  S  S  Q  S  I  V    30
                                                                       ‾‾‾‾‾‾‾‾‾‾‾‾‾‾‾‾‾‾‾
CATAGTAATGGCAACACCTATTTAGAATGGTACCTGCAGAAACCAGGCCAGTCTCCAAAGCTCCTGATCTACAAAGTTTCCAACCGATTT   180
 H  S  N  G  N  T  Y  L  E  W  Y  L  Q  K  P  G  Q  S  P  K  L  L  I  Y  K  V  S  N  R  F    60
‾‾‾‾‾‾‾‾‾‾‾‾‾‾‾‾‾‾‾‾‾‾‾‾‾                                                  ‾‾‾‾‾‾‾‾‾‾‾‾‾‾‾
   CDR1                                                                        CDR2
TCTGGGGTCCCAGACAGGTTCAGTGGCACTGGATCAGGGACAGATTTCACAGTCAGGATCAGCAGTGGAGGCTGAGGATCTGGGACTT   270
 S  G  V  P  D  R  F  S  G  S  G  S  G  T  D  F  T  V  R  I  S  R  V  E  A  E  D  L  G  L    90
 ‾
TATTACTGCTTTCAAGGTTCACGTGTTCCGTACACGTTCGGAGGGGGGACCAAGCTGGAAATAAAA                           336
 Y  Y  C  F  Q  G  S  R  V  P  Y  T  F  G  G  G  T  K  L  E  I  K                           112
          ‾‾‾‾‾‾‾‾‾‾‾‾‾‾‾‾‾‾‾‾‾‾‾
                 CDR3
```

Figure 4.

```
GTGCAGCTGCAGGAGTCAGGACCTGAGCTGGTGAAGCCTGGGGCTTCAGTGAAGATGTCCTGCAGGGCTTCACCTTCACTGAG    90
 V  Q  L  Q  E  S  G  P  E  L  V  K  P  G  A  S  V  K  M  S  C  R  A  S  G  Y  T  F  T  E     30

TATGTTATTACCTGGGTAAAACAGAGAACAGACTGGACAGGGCCTTGAGTGGATTGGAGAGATTTATCCTGGAAGTGGTAGTACTTCCTACAAT   180
 Y  V  I  T  W  V  K  Q  R  T  G  Q  G  L  E  W  I  G  E  I  Y  P  G  S  G  S  T  S  Y  N     60
         CDR1                                             CDR2

GAAAAGTTCAAGGGCAAGGCCACACTGACTGCAGACAAATCCTCAACAGCCTACATGCACCTCAGCAGCCTGACATCTGAGGACTCT          240
 E  K  F  K  G  K  A  T  L  T  A  D  K  S  S  N  T  A  Y  M  H  L  S  S  L  T  S  E  D  S     90

GCGGTCTATTTCTGTACAAGAGAGGATCTTGGGGGCCAAGGGACTCTGGTCACTGTCTCTTCA                                  333
 A  V  Y  F  C  T  R  E  D  L  G  G  Q  G  T  L  V  T  V  S  S                                  111
                     CDR3
```

Figure 5.

```
GATATCCAGCTGACCCAATCCCCAGGCACCCTGTCCCTCAGTCTGAGTCCTGGAGAGGAGCCACTCTGTCTTGCAGTCTTAGTCAGAGCATTGTG    90
 D  I  Q  L  T  Q  S  P  G  T  L  S  L  S  P  G  E  R  A  T  L  S  C  R  S  S  Q  S  I  V    30
                                                                     CDR1

CATAGTAATGGCAACACCTATTTAGAATGGTACCTGCAGAAACCAGGCCAGGCTCCAAGGCTCCTGATCTACAAAGTTTCCAACCGATTT           180
 H  S  N  G  N  T  Y  L  E  W  Y  L  Q  K  P  G  Q  A  P  R  L  L  I  Y  K  V  S  N  R  F           60
 ───────CDR1────────                                                     ─────CDR2─────

TCCGGAGTCCCAGACAGGTTCAGTGGCAGTGGATCAGGGACAGATTTCACACTTACTATCAGCAGACTGGAGCCTGAGGATTTTGCTGTG          270
 S  G  V  P  D  R  F  S  G  S  G  S  G  T  D  F  T  L  T  I  S  R  L  E  P  E  D  F  A  V          90

TATTACTGCTTTCAAGGTTCACGTGTTCCGTACGTTCGGAGGGGGGACCAAGGTGGAGATC                                       333
 Y  Y  C  F  Q  G  S  R  V  P  Y  T  F  G  G  G  T  K  V  E  I                                      113
            ──────CDR3──────
```

Figure 6.

```
GTGCAGCTGCAGCAGTCAGGAGCTGAGGTGAAAAAGCCTGGGAGCTCAGTGAAGGTCTCCTGCAAGGCTTCTGGATACACCTTCACTGAG     90
 V  Q  L  Q  Q  S  G  A  E  V  K  K  P  G  S  S  V  K  V  S  C  K  A  S  G  Y  T  F  T  E    30

TATGTTATTACCTGGGTAAAACAGAGACCTGGACAGGGTCTAGAGTGGATTGGAGAGATTTATCCTGGAAGTGGTAGTACTTCCTACAAT    180
 Y  V  I  T  W  V  K  Q  R  P  G  Q  G  L  E  W  I  G  E  I  Y  P  G  S  G  S  T  S  Y  N    60
 ─────                                                   ───────────────────────────────────
  CDR1                                                                 CDR2

GAAAAGTTCAAGGGCAAGGCCACAATCACTGCTGACAAATCCACTAACACAGCCTACATGGAGCTCAGCAGCCTGAGATCTGAGGACACT    270
 E  K  F  K  G  K  A  T  I  T  A  D  K  S  T  N  T  A  Y  M  E  L  S  S  L  R  S  E  D  T    90
 ──────

GCGTTCTATTTCTGTACAAGAGAGGATCTTGGGGGCCAAGGGGGGAGCCTCGTGGTCACCGTCTCTTCA                         333
 A  F  Y  F  C  T  R  E  D  L  G  G  Q  G  G  S  L  V  T  V  S  S                            111
              ──────────
                 CDR3
```

Figure 7.

PRODUCTION AND USE OF NOVEL PEPTIDE-BASED AGENTS FOR USE WITH BI-SPECIFIC ANTIBODIES

This application is a continuation-in-part of U.S. Ser. No. 09/337,756, filed Jun. 22, 1999, which, in turn, claims priority to Provisional Appl. Ser. Nos. 60/090,142; and 60/104,156, filed Jun. 22, 1998 and Oct. 14, 1998, respectively, the contents of which are incorporated herein by reference in their entirety.

BACKGROUND OF THE INVENTION

1. Field of the Invention

The invention relates to immunological reagents for therapeutic use, for example, in radioimmunotherapy (RAIT), and diagnostic use, for example, in radioimmunodetection (RAID) and magnetic resonance imaging (MRI). In particular, the invention relates to bi-specific antibodies (bsAbs) and bi-specific antibody fragments (bsFabs) which have at least one arm which is reactive against a targeted tissue and at least one other arm which is reactive against a linker moiety. Further, the invention relates to monoclonal antibodies that have been raised against specific immunogens, humanized and chimeric monoclonal bi-specific antibodies and antibody fragments having at least one arm which is reactive against a targeted tissue and at least one other arm which is reactive against a linker moiety, DNAs that encode such antibodies and antibody fragments, and vectors for expressing the DNAs.

2. Related Art

An approach to cancer therapy and diagnosis involves directing antibodies or antibody fragments to disease tissues, wherein the antibody or antibody fragment can target a diagnostic agent or therapeutic agent to the disease site. One approach to this methodology which has been under investigation, involves the use of bi-specific monoclonal antibodies (bsAbs) having at least one arm that is reactive against a targeted diseased tissue and at least one other arm that is reactive against a low molecular weight hapten. In this methodology, a bsAb is administered and allowed to localize to target, and to clear normal tissue. Some time later, a radiolabeled low molecular weight hapten is given, which being recognized by the second specificity of the bsAb, also localizes to the original target.

Although low MW haptens used in combination with bsAbs possess a large number of specific imaging and therapy uses, it is impractical to prepare individual bsAbs for each possible application. Further, the application of a bsAb/low MW hapten system has to contend with several other issues. First, the arm of the bsAb that binds to the low MW hapten must bind with high affinity, since a low MW hapten is designed to clear the living system rapidly, when not bound by bsAb. Second, the non-bsAb-bound low MW hapten actually needs to clear the living system rapidly to avoid non-target tissue uptake and retention. Third, the detection and/or therapy agent must remain associated with the low MW hapten throughout its application within the bsAb protocol employed.

Of interest with this approach are bsAbs that direct chelators and metal chelate complexes to cancers using Abs of appropriate dual specificity. The chelators and metal chelate complexes used are often radioactive, using radionuclides such as cobalt-57 (Goodwin et al., U.S. Pat. No. 4,863,713), indium-111 (Barbet et al., U.S. Pat. Nos. 5,256, 395 and 5,274,076, Goodwin et al., *J. Nucl. Med.* 33:1366–1372 (1992), and Kranenborg et al. *Cancer Res (suppl.)* 55:5864s–5867s (1995) and *Cancer (suppl.)* 80:2390–2397 (1997)) and gallium-68 (Boden et al., *Bioconjugate Chem.* 6:373–379, (1995) and Schuhmacher et al. *Cancer Res.* 55:115–123 (1995)) for radioimmunoimaging. Because the Abs were raised against the chelators and metal chelate complexes, they have remarkable specificity for the complex against which they were originally raised. Indeed, the bsAbs of Boden et al. have specificity for single enantiomers of enantiomeric mixtures of chelators and metal-chelate complexes. This great specificity has proven to be a disadvantage in one respect, in that other nuclides such as yttrium-90 and bismuth-213 useful for radioimmunotherapy (RAIT), and gadolinium useful for MRI, cannot be readily substituted into available reagents for alternative uses. As a result iodine-131, a non-metal, has been adopted for RAIT purposes by using an I-131-labeled indium-metal-chelate complex in the second targeting step. A second disadvantage to this methodology requires that antibodies be raised against every agent desired for diagnostic or therapeutic use.

Thus, there is a continuing need for an immunological agent which can be directed to diseased tissue and is reactive with a subsequently administered linker moiety which is bonded to or associated with a therapeutic or diagnostic metal chelate complex or a therapeutic or diagnostic chelator.

SUMMARY OF THE INVENTION

The present invention seeks to provide inter alia a bi-specific antibody or antibody fragment having at least one arm that specifically binds a targeted tissue and at least one other arm that specifically binds a targetable conjugate that can be modified for use in a wide variety of diagnostic and therapeutic applications.

Further, the invention provides pre-targeting methods of diagnosis and therapy using the combination of bi-specific antibody and the targetable conjugates:

(a) DOTA-Phe-Lys(HSG)-D-Tyr-Lys(HSG)-NH$_2$;

(b) DOTA-Phe-Lys(HSG)-Tyr-Lys(HSG)-NH$_2$; (SEQ ID NO: 15)

(c) Ac-Lys(HSG)D-Tyr-Lys(HSG)-Lys(Tscg-Cys)-NH$_2$;

(d)

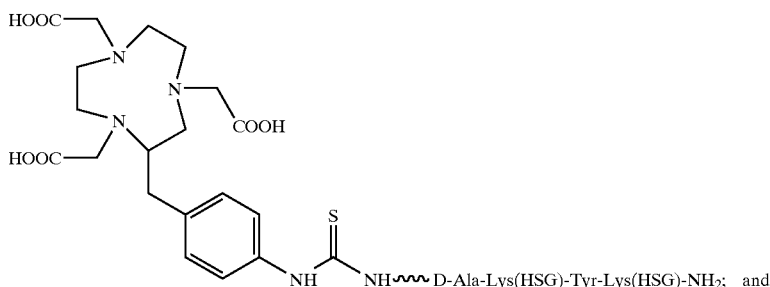

D-Ala-Lys(HSG)-Tyr-Lys(HSG)-NH₂; and (e)

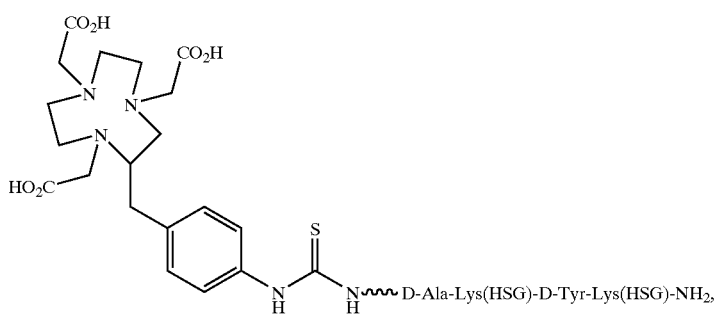

D-Ala-Lys(HSG)-D-Tyr-Lys(HSG)-NH₂, as well as methods of making the bi-specifics, and kits for use in such methods.

The present inventors have discovered that it is advantageous to raise bsAbs against a targetable conjugate that is capable of carrying one or more diagnostic or therapeutic agents. By utilizing this technique, the characteristics of the chelator, metal chelate complex, therapeutic agent or diagnostic agent can be varied to accommodate differing applications, without raising new bsAbs for each new application. Further, by using this approach, two or more distinct chelators, metal chelate complexes or therapeutic agents can be used with the inventive bsAb.

The invention relates to a method of treating or identifying diseased tissues in a subject, comprising:

(A) administering to said subject a bi-specific antibody or antibody fragment having at least one arm that specifically binds a targeted tissue and at least one other arm that specifically binds a targetable conjugate comprising at least two HSG haptens;

(B) optionally, administering to said subject a clearing composition, and allowing said composition to clear non-localized antibodies or antibody fragments from circulation;

(C) administering to said subject a targetable conjugate which comprises a carrier portion which comprises or bears at least two HSG haptens and may comprise a diagnostic or therapeutic cation, and/or one or more chelated or chemically bound therapeutic or diagnostic agents, or enzymes; and (D) when said targetable conjugate comprises an enzyme, further administering to said subject 1) a prodrug, when said enzyme is capable of converting said prodrug to a drug at the target site; or 2) a drug which is capable of being detoxified in said subject to form an intermediate of lower toxicity, when said enzyme is capable of reconverting said detoxified intermediate to a toxic form, and, therefore, of increasing the toxicity of said drug at the target site, or 3) a prodrug which is activated in said subject through natural processes and is subject to detoxification by conversion to an intermediate of lower toxicity, when said enzyme is capable of reconverting said detoxified intermediate to a toxic form, and, therefore, of increasing the toxicity of said drug at the target site.

The invention further relates to a method for detecting or treating target cells, tissues or pathogens in a mammal, comprising:

administering an effective amount of a bispecific antibody or antibody fragment comprising at least one arm that specifically binds a targeted tissue and at least one other arm that specifically binds a targetable conjugate;

wherein said at least one arm is capable of binding to a complementary binding moiety on the target cells, tissues or pathogen or on a molecule produced by or associated therewith; and administering a targetable conjugate selected from the group consisting of (a) DOTA-Phe-Lys(HSG)-D-Tyr-Lys(HSG)-NH₂;

(b) DOTA-Phe-Lys(HSG)-Tyr-Lys(HSG)-NH₂; (SEQ ID NO: 15)

(c) Ac-Lys(HSG)D-Tyr-Lys(HSG)-Lys(Tscg-Cys)-NH₂;

(d)

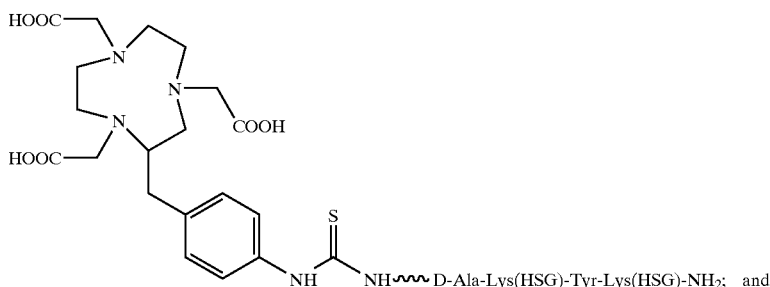

(e)

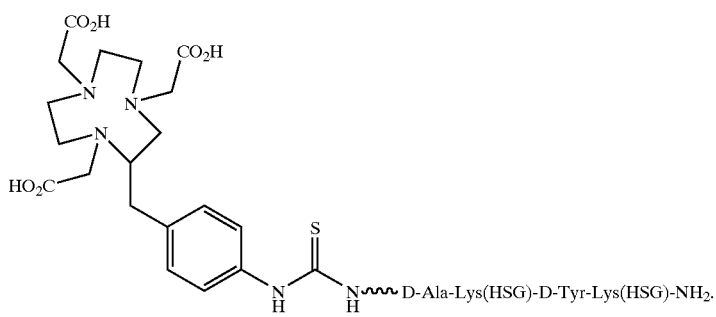

The invention further relates to a method of treating or identifying diseased tissues in a subject, comprising:

administering to said subject a bi-specific antibody or antibody fragment having at least one arm that specifically binds a targeted tissue and at least one other arm that specifically binds a targetable conjugate;

optionally, administering to said subject a clearing composition, and allowing said composition to clear non-localized antibodies or antibody fragments from circulation; and administering to said subject a targetable conjugate selected from the group consisting of:

(a) DOTA-Phe-Lys(HSG)-D-Tyr-Lys(HSG)-NH$_2$;

(b) DOTA-Phe-Lys(HSG)-Tyr-Lys(HSG)-NH$_2$; (SEQ ID NO: 15)

(c) Ac-Lys(HSG)D-Tyr-Lys(HSG)-Lys(Tscg-Cys)-NH$_2$;

(d)

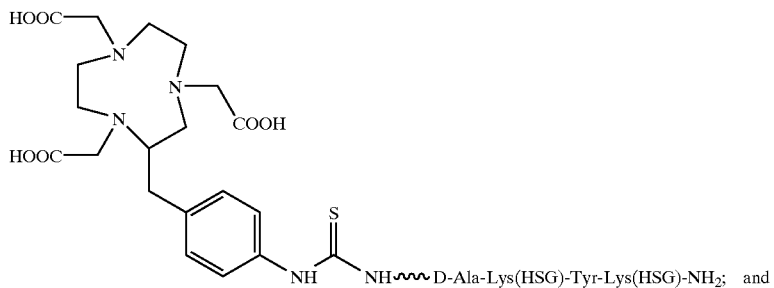

(e)

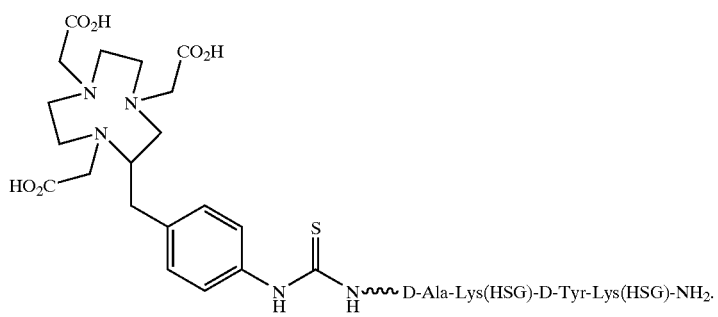

The invention further relates to a kit useful for treating or identifying diseased tissues in a subject comprising:

(A) a bi-specific antibody or antibody fragment having at least one arm that specifically binds a targeted tissue and at least one other arm that specifically binds a targetable conjugate, wherein said conjugate is selected from the group consisting of (a) DOTA-Phe-Lys(HSG)-D-Tyr-Lys(HSG)-NH$_2$;
(b) DOTA-Phe-Lys(HSG)-Tyr-Lys(HSG)-NH$_2$; (SEQ ID NO: 15)
(c) Ac-Lys(HSG)D-Tyr-Lys(HSG)-Lys(Tscg-Cys)-NH$_2$;

(d)
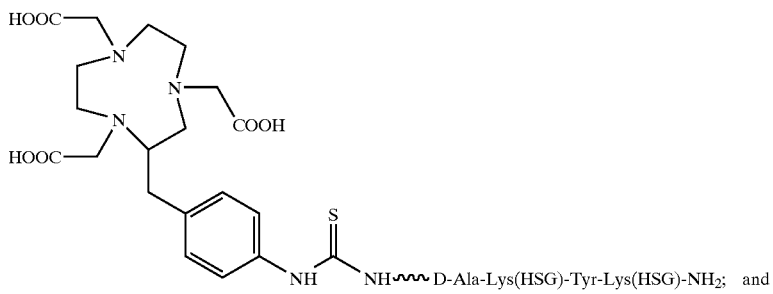

(e)
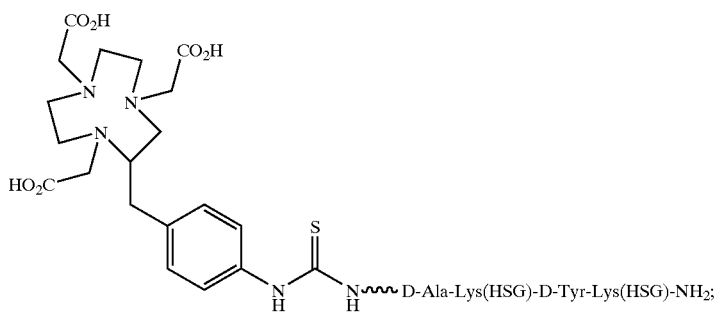

(B) a targetable conjugate which comprises a carrier portion which comprises or bears at least one epitope recognizable by said at least one other arm of said bi-specific antibody or antibody fragment, and one or more conjugated therapeutic or diagnostic agents, or enzymes; and (C) optionally, a clearing composition useful for clearing non-localized antibodies and antibody fragments; and (D) optionally, when said first targetable conjugate comprises an enzyme, 1) a prodrug, when said enzyme is capable of converting said prodrug to a drug at the target site; or 2) a drug which is capable of being detoxified in said subject to form an intermediate of lower toxicity, when said enzyme is capable of reconverting said detoxified intermediate to a toxic form, and, therefore, of increasing the toxicity of said drug at the target site, or 3) a prodrug which is activated in said subject through natural processes and is subject to detoxification by conversion to an intermediate of lower toxicity, when said enzyme is capable of reconverting said detoxified intermediate to a toxic form, and, therefore, of increasing the toxicity of said drug at the target site.

The invention further relates to a targetable conjugate selected from the group consisting of:

(a) DOTA-Phe-Lys(HSG)-D-Tyr-Lys(HSG)-NH$_2$;
(b) DOTA-Phe-Lys(HSG)-Tyr-Lys(HSG)-NH$_2$; (SEQ ID NO: 15)
(c) Ac-Lys(HSG)D-Tyr-Lys(HSG)-Lys(Tscg-Cys)-NH$_2$;

(d)
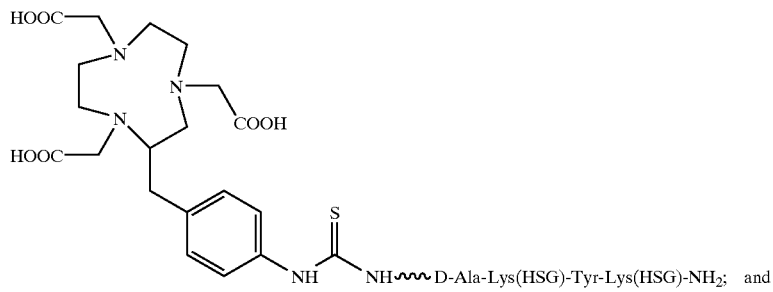

(e)

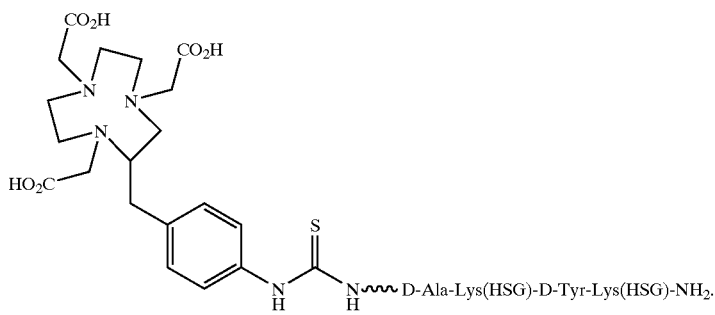

The invention further relates to a method of screening for a targetable conjugate comprising:

contacting said targetable construct with a bi-specific antibody or antibody fragment having at least one arm that specifically binds a targeted tissue and at least one other arm that specifically binds said targetable conjugate to give a mixture;

(d)

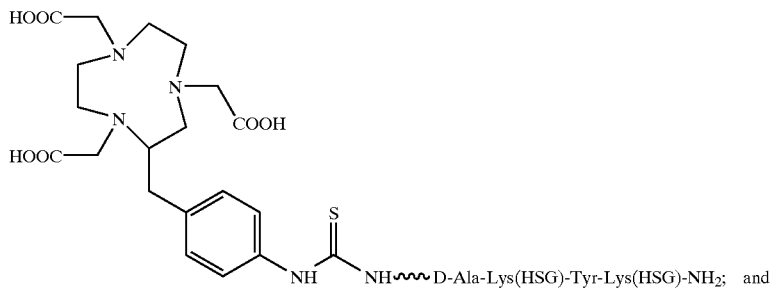

(e)

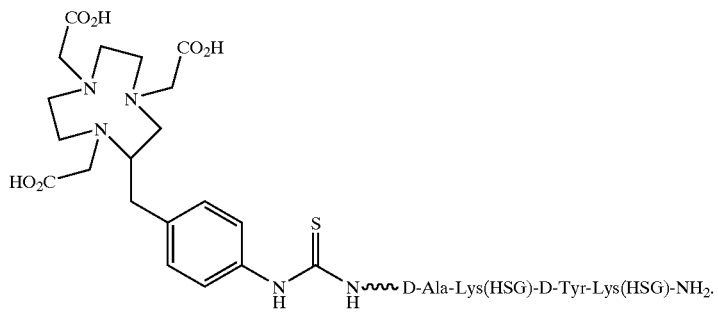

wherein said at least one arm is capable of binding to a complementary binding moiety on the target cells, tissues or pathogen or on a molecule produced by or associated therewith; and optionally incubating said mixture; and analyzing said mixture.

The invention further relates to a method for imaging normal tissue in a mammal, comprising:

administering an effective amount of a bispecific antibody or antibody fragment comprising at least one arm that specifically binds a targeted tissue and at least one other arm that specifically binds a targetable conjugate;

wherein said at least one arm is capable of binding to a complementary binding moiety on the target cells, tissues or pathogen or on a molecule produced by or associated therewith; and administering a targetable conjugate selected from the group consisting of (a) DOTA-Phe-Lys(HSG)-D-Tyr-Lys(HSG)-NH$_2$;

(b) DOTA-Phe-Lys(HSG)-Tyr-Lys(HSG)-NH$_2$; (SEQ ID NO: 15)

(c) Ac-Lys(HSG)D-Tyr-Lys(HSG)-Lys(Tscg-Cys)-NH$_2$;

The invention further relates to a method of intraoperatively identifying diseased tissues, in a subject, comprising:

administering an effective amount of a bispecific antibody or antibody fragment comprising at least one arm that specifically binds a targeted tissue and at least one other arm that specifically binds a targetable conjugate;

wherein said at least one arm is capable of binding to a complementary binding moiety on the target cells, tissues or pathogen or on a molecule produced by or associated therewith; and administering a targetable conjugate selected from the group consisting of (a) DOTA-Phe-Lys(HSG)-D-Tyr-Lys(HSG)-NH$_2$;

(b) DOTA-Phe-Lys(HSG)-Tyr-Lys(HSG)-NH$_2$; (SEQ ID NO: 15)

(c) Ac-Lys(HSG)D-Tyr-Lys(HSG)-Lys(Tscg-Cys)-NH$_2$;

(d)

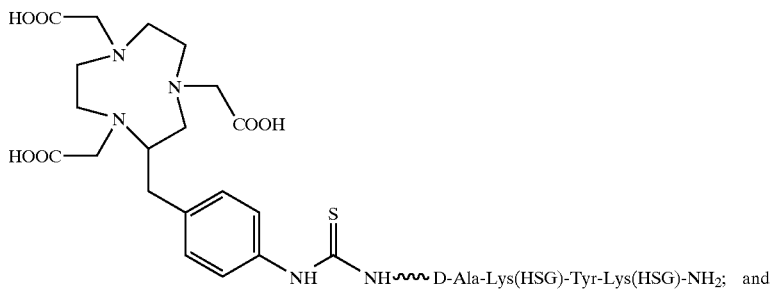

(e)

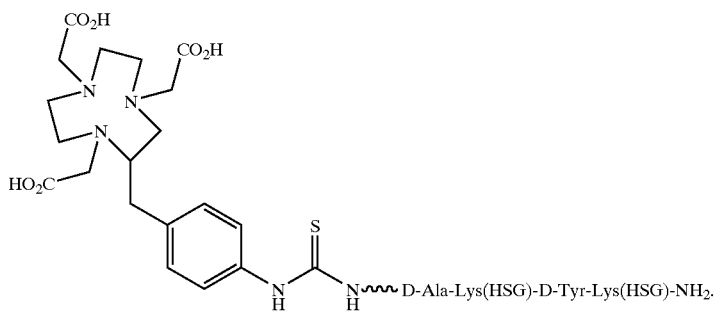

The invention further relates to a method for the endoscopic identification of diseased tissues, in a subject, comprising:

administering an effective amount of a bispecific antibody or antibody fragment comprising at least one arm that specifically binds a targeted tissue and at least one other arm that specifically binds a targetable conjugate;

wherein said at least one arm is capable of binding to a complementary binding moiety on the target cells, tissues or pathogen or on a molecule produced by or associated therewith; and administering a targetable conjugate selected from the group consisting of (a) DOTA-Phe-Lys(HSG)-D-Tyr-Lys(HSG)-NH$_2$;

(b) DOTA-Phe-Lys(HSG)-Tyr-Lys(HSG)-NH$_2$; (SEQ ID NO: 15)

(c) Ac-Lys(HSG)D-Tyr-Lys(HSG)-Lys(Tscg-Cys)-NH$_2$;

(d)

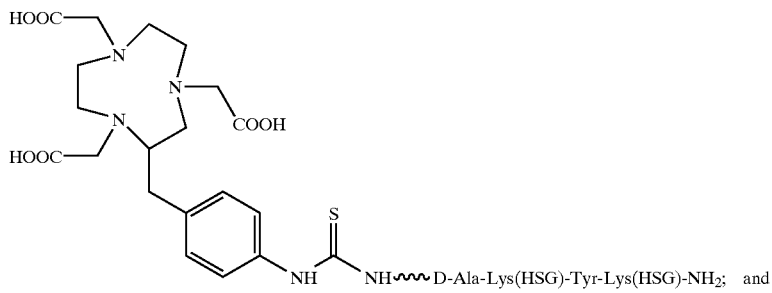

(e)

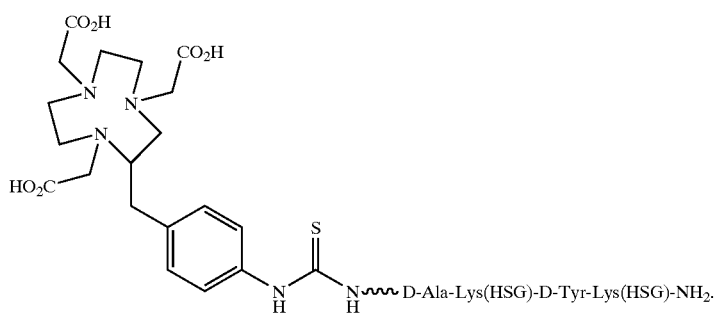

The intenvtion further relates to a method for the intravascular identification of diseased tissues, in a subject, comprising:

administering an effective amount of a bispecific antibody or antibody fragment comprising at least one arm that specifically binds a targeted tissue and at least one other arm that specifically binds a targetable conjugate;

wherein said at least one arm is capable of binding to a complementary binding moiety on the target cells, tissues or pathogen or on a molecule produced by or associated therewith; and administering a targetable conjugate selected from the group consisting of (a) DOTA-Phe-Lys(HSG)-D-Tyr-Lys(HSG)-NH$_2$;
(b) DOTA-Phe-Lys(HSG)-Tyr-Lys(HSG)-NH$_2$; (SEQ ID NO: 15)
(c) Ac-Lys(HSG)D-Tyr-Lys(HSG)-Lys(Tscg-Cys)-NH$_2$;

(d)
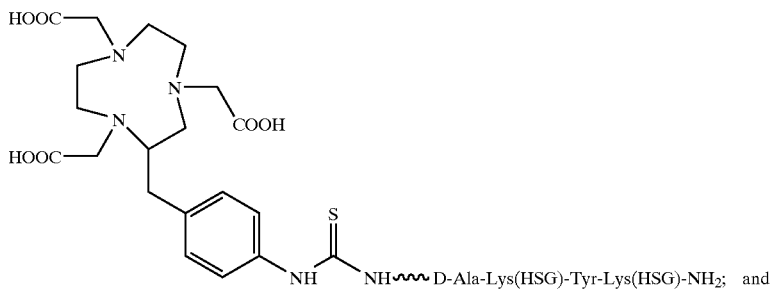
D-Ala-Lys(HSG)-Tyr-Lys(HSG)-NH$_2$; and (e)
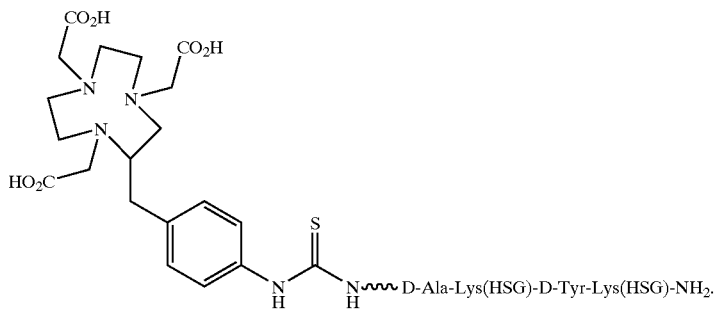
D-Ala-Lys(HSG)-D-Tyr-Lys(HSG)-NH$_2$.

treating or identifying diseased tissue. Examples of conjugated agents include, but are not limited to, chelators, metal chelate complexes, drugs, toxins (e.g., ricin, abrin, ribonuclease, DNase I, *Staphylococcal* enterotoxin-A, pokeweed antiviral protein, gelonin, diphtherin toxin, *Pseudomonas* exotoxin, *Pseudomonas* endotoxin) and other effector molecules. Additionally, enzymes useful for activating a prodrug or increasing the target-specific toxicity of a drug can be conjugated to the targetable construct. Thus, the use of bsAb which are reactive to a targetable construct allows a variety of therapeutic and diagnostic applications to be performed without raising new bsAb for each application.

Additionally, the present invention encompasses a method for detecting or treating target cells, tissues or pathogens in a mammal, comprising administering an effective amount of a bispecific antibody or antibody fragment comprising at least one arm that specifically binds a targeted tissue and at least one other arm that specifically binds a targetable conjugate. As used herein, the term "pathogen" includes, but is not limited to fungi, viruses (e.g., human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus and blue tongue virus), parasites and bacteria (e.g., *Streptococcus agalactiae, Legionella pneumophilia, Streptococcus pyogenes, Escherichia coli, Neisseria gonorrhoeae, Neisseria meningitidis, Pneumococcus, Hemophilis influenzae B, Treponema pallidum*, Lyme disease spirochetes, *Pseudomonas aeruginosa, Mycobacterium leprae, Brucella abortus, Mycobacterium tuberculosis* and Tetanus toxin). See U.S. Pat. No. 5,332,567.

The present invention encompasses antibodies and antibody fragments. The antibody fragments are antigen binding

BRIEF DESCRIPTION OF THE DRAWINGS

FIGS. 1–7 show the polypeptide sequence for MAb 679 V$_k$ (SEQ ID NOS 1–2), MAb 679 V$_h$ (SEQ ID NOS 3–4), MAb 679 scFv (SEQ ID NOS 5–6), Mu9 V$_k$ (SEQ ID NOS 7–8), Mu9 V$_h$ (SEQ ID NOS 9–10), hMu9 V$_k$ (SEQ ID NOS 11–12), and hMu9 V$_h$ (SEQ ID NOS 13–14), respectively. The corresponding polynucleotide which codes for said polypeptides are also shown in FIGS. 1–7.

DETAILED DESCRIPTION

I. Overview

The present invention provides a bi-specific antibody or antibody fragment having at least one arm that is reactive against a targeted tissue and at least one other arm that is reactive against a targetable construct. The targetable construct is comprised of a carrier portion and at least 2 units of a recognizable hapten. Examples of recognizable haptens include, but are not limited to, histamine succinyl glycine (HSG) and fluorescein isothiocyanate. The targetable construct may be conjugated to a variety of agents useful for portions of an antibody, such as F(ab')₂, F(ab)₂, Fab', Fab, and the like. The antibody fragments bind to the same antigen that is recognized by the intact antibody. For example, an anti-CD22 monoclonal antibody fragment binds to an epitope of CD22.

The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("sFv proteins"), and minimal recognition units consisting of the amino acid residues that mimic the "hypervariable region." Three of these so-called "hypervariable" regions or "complementarity-determining regions" (CDR) are found in each variable region of the light or heavy chain. Each CDR is flanked by relatively conserved framework regions (FR). The FR are thought to maintain the structural integrity of the variable region. The CDRs of a light chain and the CDRs of a corresponding heavy chain form the antigen-binding site. The "hypervariability" of the CDRs accounts for the diversity of specificity of antibodies.

As used herein, the term "subject" refers to any animal (i.e., vertebrates and invertebrates) including, but not limited to humans and other primates, rodents (e.g., mice, rats, and guinea pigs), lagamorphs (e.g., rabbits), bovines (e.g, cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc.), as well as feral or wild animals, including, but not limited to, such animals as ungulates (e.g., deer), bear, fish, lagamorphs, rodents, birds, etc. It is not intended that the term be limited to a particular age or sex. Thus, adult and newborn subjects, as well as fetuses, whether male or female, are encompassed by the term.

II. Constructs Targetable to Antibodies

The targetable construct can be of diverse structure, but is selected not only to elicit sufficient immune responses, but also for rapid in vivo clearance when used within the bsAb targeting method. Hydrophobic agents are best at eliciting strong immune responses, whereas hydrophilic agents are preferred for rapid in vivo clearance, thus, a balance between hydrophobic and hydrophilic needs to be established. This is accomplished, in part, by relying on the use of hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic. Aside from peptides, carbohydrates may be used.

Peptides having as few as two amino-acid residues may be used, preferably two to ten residues, if also coupled to other moieties such as chelating agents. The linker should be a low molecular weight conjugate, preferably having a molecular weight of less than 50,000 daltons, and advantageously less than about 20,000 daltons, 10,000 daltons or 5,000 daltons, including the metal ions in the chelates. For instance, the known peptide DTPA-Tyr-Lys(DTPA)-OH (wherein DTPA is diethylenetriaminepentaacetic acid) has been used to generate antibodies against the indium-DTPA portion of the molecule. However, by use of the non-indium-containing molecule, and appropriate screening steps, new Abs against the tyrosyl-lysine dipeptide can be made. More usually, the antigenic peptide will have four or more residues, such as the peptide DOTA-Phe-Lys(HSG)-Tyr-Lys (HSG)-NH₂ (SEQ ID NO: 15). wherein DOTA is 1,4,7,10-tetraazacyclododecanetetraacetic acid and HSG is the histamine succinyl glycyl group of the formula:

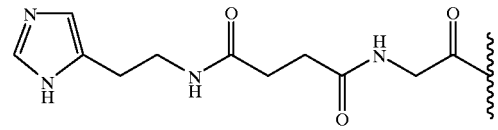

The non-metal-containing peptide may be used as an immunogen, with resultant Abs screened for reactivity against the Phe-Lys-Tyr-Lys (SEQ ID NO: 18) backbone.

The invention also contemplates the incorporation of unnatural amino acids, e.g., D-amino acids, into the backbone structure to ensure that, when used with the final bsAb/linker system, the arm of the bsAb which recognizes the linker moiety is completely specific. The invention further contemplates other backbone structures such as those constructed from non-natural amino acids and peptoids.

The peptides to be used as immunogens are synthesized conveniently on an automated peptide synthesizer using a solid-phase support and standard techniques of repetitive orthogonal deprotection and coupling. Free amino groups in the peptide, that are to be used later for chelate conjugation, are advantageously blocked with standard protecting groups such as an acetyl group. Such protecting groups will be known to the skilled artisan. See Greene and Wuts *Protective Groups in Organic Synthesis*, 1999 (John Wiley and Sons, N.Y.). When the peptides are prepared for later use within the bsAb system, they are advantageously cleaved from the resins to generate the corresponding C-terminal amides, in order to inhibit in vivo carboxypeptidase activity.

The haptens of the immunogen comprise an immunogenic recognition moiety, for example, a chemical hapten. Using a chemical hapten, preferably the HSG hapten, high specificity of the linker for the antibody is exhibited. This occurs because antibodies raised to the HSG hapten are known and can be easily incorporated into the appropriate bispecific antibody. Thus, binding of the linker with the attached hapten would be highly specific for the antibody or antibody fragment.

III. Chelate Moieties

The presence of hydrophilic chelate moieties on the linker moieties helps to ensure rapid in vivo clearance. In addition to hydrophilicity, chelators are chosen for their metal-binding properties, and are changed at will since, at least for those linkers whose bsAb epitope is part of the peptide or is a non-chelate chemical hapten, recognition of the metal-chelate complex is no longer an issue.

Particularly useful metal-chelate combinations include 2-benzyl-DTPA and its monomethyl and cyclohexyl analogs, used with $^{47}$Sc, $^{52}$Fe, $^{55}$Co, $^{67}$Ga, $^{68}$Ga, $^{111}$In, $^{89}$Zr, $^{90}$Y, $^{161}$Tb, $^{177}$Lu, $^{212}$Bi, $^{213}$Bi, and $^{225}$Ac for radio-imaging and RAIT. The same chelators, when complexed with non-radioactive metals, such as Mn, Fe and Gd can be used for MRI, when used along with the bsAbs of the invention. Macrocyclic chelators such as NOTA (1,4,7-triaza-cyclononane-N,N',N"-triacetic acid), DOTA, and TETA (p-bromoacetamido-benzyl-tetraethylaminetetraacetic acid) are of use with a variety of metals and radiometals, most particularly with radionuclides of Ga, Y and Cu, respectively.

DTPA and DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers are of interest for stably binding nuclides such as $^{223}$Ra for RAIT. Porphyrin chelators may be used with numerous radiometals, and are also useful as certain cold metal complexes for bsAb-directed immuno-phototherapy. More than one type of chelator may be conjugated to a carrier to bind multiple metal ions, e.g., cold ions, diagnostic radionuclides and/or therapeutic radionuclides. Particularly useful therapeutic radionuclides include, but are not limited to $^{32}$P, $^{33}$P, $^{47}$Sc, $^{64}$Cu, $^{67}$Cu, $^{67}$Ga, $^{90}$Y, $^{111}$Ag, $^{111}$In, $^{125}$I, $^{131}$I, $^{142}$Pr, $^{153}$Sm, $^{161}$Tb, $^{166}$Dy, $^{166}$Ho, $^{177}$Lu, $^{186}$Re, $^{188}$Re, $^{189}$Re, $^{212}$Pb, $^{212}$Bi, $^{213}$Bi, $^{211}$At, $^{223}$Ra and $^{225}$Ac. Particularly useful diagnostic radionuclides include, but are not limited to, $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc $^{111}$In, $^{123}$I, $^{124}$I, $^{125}$I, $^{131}$I, $^{154-158}$Gd and $^{175}$Lu.

Chelators such as those disclosed in U.S. Pat. No. 5,753, 206, especially thiosemicarbazonylglyoxylcysteine(Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands, especially sulfur- or phosphorus-containing ligands. It can be preferentially to the thiol-containing Tscg-Cys. Other hard acid chelators such as NOTA, DOTA, TETA and the like can be substituted for the DTPA groups, and Mabs specific to them can be produced using analogous techniques to those used to generate the anti-di-DTPA Mab.

It will be appreciated that two different hard acid or soft acid chelators can be incorporated into the linker, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be radioactive or useful for MRI enhancement, to be incorporated into a linker for eventual capture by a pretargeted bsAb.

Preferred chelators include NOTA, DOTA and Tscg and combinations thereof These chelators have been incorporated into a chelator-peptide conjugate motif as exemplified in the following constructs:

(a) DOTA-Phe-Lys(HSG)-D-Tyr-Lys(HSG)-NH$_2$;

(b) DOTA-Phe-Lys(HSG)-Tyr-Lys(HSG)-NH$_2$; (SEQ ID NO: 15)

(c) Ac-Lys(HSG)D-Tyr-Lys(HSG)-Lys(Tscg-Cys)-NH$_2$;

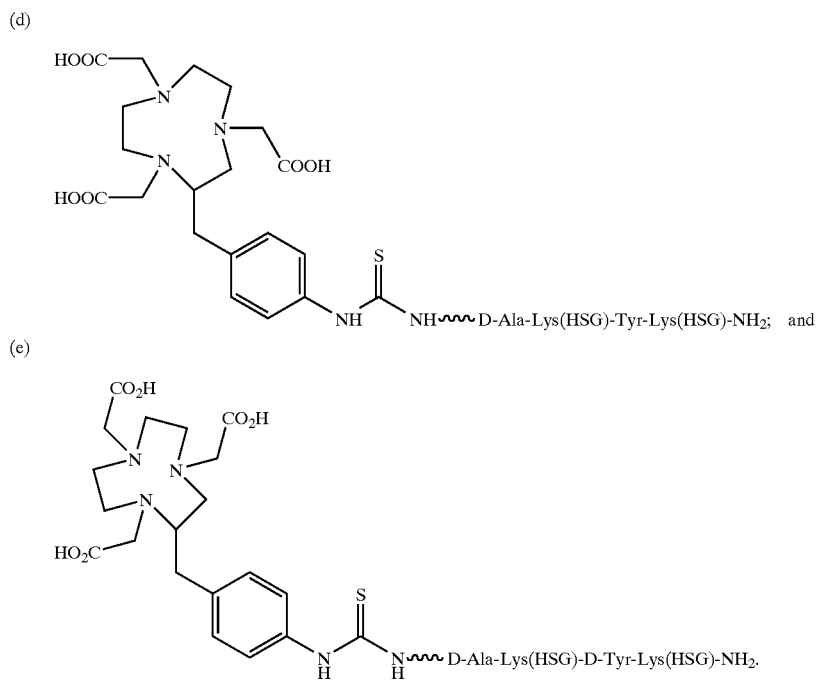

useful to link more than one type of chelator to a peptide, e.g., a DTPA or similar chelator for, say In(III) cations, and a thiol-containing chelator, e.g., Tscg-Cys, for Tc cations. Because antibodies to a di-DTPA hapten are known (Barbet '395, supra) and are readily coupled to a targeting antibody to form a bsAb, it is possible to use a peptide hapten with cold diDTPA chelator and another chelator for binding a radioisotope, in a pretargeting protocol, for targeting the radioisotope. One example of such a peptide is Ac-Lys (DTPA)-Tyr-Lys(DTPA)-Lys(Tscg-Cys-)-NH$_{12}$ (SEQ ID NO: 16). This peptide can be preloaded with In(III) and then labeled with 99-m-Tc cations, the In(III) ions being preferentially chelated by the DTPA and the Tc cations binding The chelator-peptide conjugates (d) and (e), above, has been shown to bind $^{68}$Ga and is thus useful in positron emission tomography (PET) applications.

Chelators are coupled to the linker moieties using standard chemistries which are discussed more fully in the working Examples below. Briefly, the synthesis of the peptide Ac-Lys(HSG)D-Tyr-Lys(HSG)-Lys(Tscg-Cys-)-NH$_2$ was accomplished by first attaching Aloc-Lys(Fmoc)-OH to a Rink amide resin on the peptide synthesizer. The protecting group abbreviations "Aloc" and "Fmoc" used herein refer to the groups allyloxycarbonyl and fluorenyl-methyloxy carbonyl. The Fmoc-Cys(Trt)-OH and TscG were then added to the side chain of the lysine using standard Fmoc automated synthesis protocols to form the following peptide: Aloc-Lys(Tscg-Cys(Trt)-rink resin. The Aloc group was then removed. The peptide synthesis was then continued on the synthesizer to make the following peptide: (Lys(Aloc)-D-Tyr-Lys(Aloc)-Lys(Tscg-Cys(Trt)-)-)-rink resin. Following N-terminus acylation, and removal of the side chain Aloc protecting groups. The resulting peptide was then treated with activated N-trityl-HSG-OH until the resin gave a negative test for amines using the Kaiser test. See Karacay et al. *Bioconjugate Chem.* 11:842–854 (2000). The synthesis of Ac-Lys(HSG)D-Tyr-Lys(HSG)-Lys(Tscg-Cys-)-NH$_2$, as well as the syntheses of DOTA-Phe-Lys(HSG)-D-Tyr-Lys(HSG)-NH$_2$; and DOTA-Phe-Lys(HSG)-Tyr-Lys(HSG)-NH$_2$ (SEQ ID NO: 15) are described in greater detail below.

IV. General Methods for Preparation of Metal Chelates

Chelator-peptide conjugates may be stored for long periods as solids. They may be metered into unit doses for metal-binding reactions, and stored as unit doses either as solids, aqueous or semi-aqueous solutions, frozen solutions or lyophilized preparations. They may be labeled by well-known procedures. Typically, a hard acid cation is introduced as a solution of a convenient salt, and is taken up by the hard acid chelator and possibly by the soft acid chelator. However, later addition of soft acid cations leads to binding thereof by the soft acid chelator, displacing any hard acid cations which may be chelated therein. For example, even in the presence of an excess of cold $^{111}$InCl$_3$, labeling with 99m-Tc(V) glucoheptonate or with Tc cations generated in situ with stannous chloride and Na99m-TcO$_4$ proceeds quantitatively on the soft acid chelator. Other soft acid cations such as $^{186}$Re, $^{188}$Re, $^{213}$Bi and divalent or trivalent cations of Mn, Co, Ni, Pb, Cu, Cd, Au, Fe, Ag (monovalent), Zn and Hg, especially $^{64}$Cu and $^{67}$Cu, and the like, some of which are useful for radioimmunodiagnosis or radioimmunotherapy, can be loaded onto the linker peptide by analogous methods. Re cations also can be generated in situ from perrhenate and stannous ions or a prereduced rhenium glucoheptonate or other transchelator can be used. Because reduction of perrhenate requires more stannous ion (typically above 200 µg/mL final concentration) than is needed for the reduction of Tc, extra care needs to be taken to ensure that the higher levels of stannous ion do not reduce sensitive disulfide bonds such as those present in disulfide-cyclized peptides. During radiolabeling with rhenium, similar procedures are used as are used with the Tc-99m. A preferred method for the preparation of ReO metal complexes of the Tscg-Cys-ligands is by reacting the peptide with ReOCl$_3$(P(Ph$_3$)$_2$ but it is also possible to use other reduced species such as ReO(ethylenediamine)$_2$.

V. Methods of Administration

It should be noted that much of the discussion presented hereinbelow focuses on the use of the inventive bispecific antibodies and targetable constructs in the context of treating diseased tissue. The invention contemplates, however, the use of the inventive bispecific antibodies and targetable constructs in treating and/or imaging normal tissue and organs using the methods described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210. As used herein, the term "tissue" refers to tissues, including but not limited to, tissues from the ovary, thymus, parathyroid or spleen.

The administration of a bsAb and a therapeutic agent associated with the linker moieties discussed above may be conducted by administering the bsAb at some time prior to administration of the therapeutic agent which is associated with the linker moiety. The doses and timing of the reagents can be readily devised by a skilled artisan, and are dependent on the specific nature of the reagents employed. If a bsAb-F(ab')$_2$ derivative is given first, then a waiting time of 24–72 hr before administration of the linker moiety would be appropriate. If an IgG-Fab' bsAb conjugate is the primary targeting vector, then a longer waiting period before administration of the linker moiety would be indicated, in the range of 3–10 days.

As used herein, the term "therapeutic agent" includes, but is not limited to a drug, prodrug and/or toxin. The terms "drug," "prodrug," and "toxin" are defined throughout the specification.

After sufficient time has passed for the bsAb to target to the diseased tissue, the diagnostic agent is administered. Subsequent to administration of the diagnostic agent, imaging can be performed. Tumors can be detected in body cavities by means of directly or indirectly viewing various structures to which light of the appropriate wavelength is delivered and then collected. Lesions at any body site can be viewed so long as nonionizing radiation can be delivered and recaptured from these structures. For example, PET which is a high resolution, non-invasive, imaging technique can be used with the inventive antibodies for the visualization of human disease. In PET, 511 keV gamma photons produced during positron annihilation decay are detected.

The invention generally contemplates the use of diagnostic agents which emit 25–600 keV gamma particles and/or positrons. Examples of such agents include, but are not limited to $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, $^{123}$I, $^{124}$I, $^{125}$I, $^{131}$I, $^{154-158}$Gd and $^{175}$Lu.

The present antibodies or antibody fragments can be used in a method of photodynamic therapy (PDT) as discussed in U.S. Pat. Nos. 6,096,289; 4,331,647; 4,818,709; 4,348,376; 4,361,544; 4,444,744; 5,851,527.

In PDT, a photosensitizer, e.g., a hematoporphyrin derivative such as dihematoporphyrin ether, is administered to a subject. Anti-tumor activity is initiated by the use of light, e.g., 630 nm. Alternate photosensitizers can be utilized, including those useful at longer wavelengths, where skin is less photosensitized by the sun. Examples of such photosensitizers include, but are not limited to, benzoporphyrin monoacid ring A (BPD-MA), tin etiopurpurin (SnET2), sulfonated aluminum phthalocyanine (AlSPc) and lutetium texaphyrin (Lutex).

Additionally, in PDT, a diagnostic agent is injected, for example, systemically, and laser-induced fluorescence can be used by endoscopes to detect sites of cancer which have accreted the light-activated agent. For example, this has been applied to fluorescence bronchoscopic disclosure of early lung tumors. Doiron et al. *Chest* 76:32 (1979). In another example, the antibodies and antibody fragments can be used in single photon emission. For example, a Tc-99m-labeled diagnostic agent can be administered to a subject following administration of the inventive antibodies or antibody fragments. The subject is then scanned with a gamma camera which produces single-photon emission computed tomographic images and defines the lesion or tumor site.

Therapeutically useful immunoconjugates can be obtained by conjugating photoactive agents or dyes to an antibody composite. Fluorescent and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), *Photodynamic Therapy of Tumors and Other*

Diseases (Libreria Progetto 1985); van den Bergh, *Chem. Britain* 22:430 (1986)). Moreover, monoclonal antibodies have been coupled with photoactivated dyes for achieving phototherapy. Mew et al., *J. Immunol.* 130:1473 (1983); idem., *Cancer Res.* 45:4380 (1985); Oseroff et al., *Proc. Natl. Acad. Sci. USA* 83:8744 (1986); idem., *Photochem. Photobiol.* 46:83 (1987); Hasan et al., *Prog. Clin. Biol. Res.* 288:471 (1989); Tatsuta et al., *Lasers Surg. Med.* 9:422 (1989); Pelegrin et al., *Cancer* 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes.

The linker moiety may also be conjugated to an enzyme capable of activating a prodrug at the target site or improving the efficacy of a normal therapeutic by controlling the body's detoxification pathways. Following administration of the bsAb, an enzyme conjugated to the linker moiety, a low MW hapten recognized by the second arm of the bsAb, is administered. After the enzyme is pretargeted to the target site, a cytotoxic drug is injected, which is known to act at the target site. The drug may be one which is detoxified by the mammal's ordinary detoxification processes. For example, the drug may be converted into the potentially less toxic glucuronide in the liver. The detoxified intermediate can then be reconverted to its more toxic form by the pretargeted enzyme at the target site. Alternatively, an administered prodrug can be converted to an active drug by the pretargeted enzyme. The pretargeted enzyme improves the efficacy of the treatment by recycling the detoxified drug. This approach can be adopted for use with any enzyme-drug pair.

Certain cytotoxic drugs that are useful for anticancer therapy are relatively insoluble in serum. Some are also quite toxic in an unconjugated form, and their toxicity is considerably reduced by conversion to prodrugs. Conversion of a poorly soluble drug to a more soluble conjugate, e.g., a glucuronide, an ester of a hydrophilic acid or an amide of a hydrophilic amine, will improve its solubility in the aqueous phase of serum and its ability to pass through venous, arterial or capillary cell walls and to reach the interstitial fluid bathing the tumor. Cleavage of the prodrug deposits the less soluble drug at the target site. Many examples of such prodrug-to-drug conversions are disclosed in Hansen U.S. Pat. No. 5,851,527.

Conversion of certain toxic substances such as aromatic or alicyclic alcohols, thiols, phenols and amines to glucuronides in the liver is the body's method of detoxifying them and making them more easily excreted in the urine. One type of antitumor drug that can be converted to such a substrate is epirubicin, a 4-epimer of doxorubicin (Adriamycin), which is an anthracycline glycoside and has been shown to be a substrate for human beta-D-glucuronidase See, e.g., Arcamone *Cancer Res.* 45:5995 (1985). Other analogues with fewer polar groups are expected to be more lipophilic and show greater promise for such an approach. Other drugs or toxins with aromatic or alicyclic alcohol, thiol or amine groups are candidates for such conjugate formation. These drugs, or other prodrug forms thereof, are suitable candidates for the site-specific enhancement methods of the present invention.

The prodrug CPT-11 (irinotecan) is converted in vivo by carboxylesterase to the active metabolite SN-38. One application of the invention, therefore, is to use a bsAb targeted against a tumor and a hapten (e.g. di-DTPA) followed by injection of a di-DTPA-carboxylesterase conjugate. Once a suitable tumor-to-background localization ratio has been achieved, the CPT-11 is given and the tumor-localized carboxylesterase serves to convert CPT-11 to SN-38 at the tumor. Due to its poor solubility, the active SN-38 will remain in the vicinity of the tumor and, consequently, will exert an effect on adjacent tumor cells that are negative for the antigen being targeted. This is a further advantage of the method. Modified forms of carboxylesterases have been described and are within the scope of the invention. See, e.g., Potter et al., *Cancer Res.* 58:2646–2651 (1998) and Potter et al., *Cancer Res.* 58:3627–3632 (1998).

Etoposide is a widely used cancer drug that is detoxified to a major extent by formation of its glucuronide and is within the scope of the invention. See, e.g., Hande et al. *Cancer Res.* 48:1829–1834 (1988). Glucuronide conjugates can be prepared from cytotoxic drugs and can be injected as therapeutics for tumors pre-targeted with mAb-glucuronidase conjugates. See, e.g., Wang et al. *Cancer Res.* 52:4484–4491 (1992). Accordingly, such conjugates also can be used with the pre-targeting approach described here. Similarly, designed prodrugs based on derivatives of daunomycin and doxorubicin have been described for use with carboxylesterases and glucuronidases. See, e.g., Bakina et al. *J. Med Chem.* 40:4013–4018 (1997). Other examples of prodrug/enzyme pairs that can be used within the present invention include, but are not limited to, glucuronide prodrugs of hydroxy derivatives of phenol mustards and beta-glucuronidase; phenol mustards or CPT-11 and carboxypeptidase; methotrexate-substituted alpha-amino acids and carboxypeptidase A; penicillin or cephalosporin conjugates of drugs such as 6-mercaptopurine and doxorubicin and beta-lactamase; etoposide phosphate and alkaline phosphatase.

The enzyme capable of activating a prodrug at the target site or improving the efficacy of a normal therapeutic by controlling the body's detoxification pathways may aternatively be conjugated to the hapten. The enzyme-hapten conjugate is administered to the subject following administration of the pre-targeting bsAb and is directed to the target site. After the enzyme is localized at the target site, a cytotoxic drug is injected, which is known to act at the target site, or a prodrug form thereof which is converted to the drug in situ by the pretargeted enzyme. As discussed above, the drug is one which is detoxified to form an intermediate of lower toxicity, most commonly a glucuronide, using the mammal's ordinary detoxification processes. The detoxified intermediate, e.g., the glucuronide, is reconverted to its more toxic form by the pretargeted enzyme and thus has enhanced cytotoxicity at the target site. This results in a recycling of the drug. Similarly, an administered prodrug can be converted to an active drug through normal biological processess. The pretargeted enzyme improves the efficacy of the treatment by recycling the detoxified drug. This approach can be adopted for use with any enzyme-drug pair.

The invention further contemplates the use of the inventive bsAb and the diagnostic agent(s) in the context of Boron Neutron Capture Therapy (BNCT) protocols. BNCT is a binary system designed to deliver ionizing radiation to tumor cells by neutron irradiation of tumor-localized $^{10}B$ atoms. BNCT is based on the nuclear reaction which occurs when a stable isotope, isotopically enriched $^{10}B$ (present in 19.8% natural abundance), is irradiated with thermal neutrons to produce an alpha particle and a $^7Li$ nucleus. These particles have a path length of about one cell diameter, resulting in high linear energy transfer. Just a few of the short-range 1.7 MeV alpha particles produced in this nuclear reaction are sufficient to target the cell nucleus and destroy it. Success with BNCT of cancer requires methods for localizing a high concentration of $^{10}$B at tumor sites, while leaving non-target organs essentially boron-free. Compositions and methods for treating tumors in subjects using pre-targeting bsAb for BNCT are described in co-pending patent appl. Ser. No. 09/205,243, now U.S. Pat. No. 6,228,362, and can easily be modified for the purposes of the present invention.

It should also be noted that a bispecific antibody or antibody fragment can be used in the present method, with at least one binding site specific to an antigen at a target site and at least one other binding site specific to the enzyme component of the antibody-enzyme conjugate. Such an antibody can bind the enzyme prior to injection, thereby obviating the need to covalently conjugate the enzyme to the antibody, or it can be injected and localized at the target site and, after non-targeted antibody has substantially cleared from the circulatory system of the mammal, enzyme can be injected in an amount and by a route which enables a sufficient amount of the enzyme to reach a localized antibody or antibody fragment and bind to it to form the antibody-enzyme conjugate in situ.

It should also be noted that the invention also contemplates the use of multivalent target binding proteins which have at least three different target binding sites as described in patent application Ser. No. 60/220,782. Multivalent target binding proteins have been made by cross-linking several Fab-like fragments via chemical linkers. See U.S. Pat. Nos. 5,262,524; 5,091,542 and Landsdorp et al. *Euro. J. Immunol.* 16: 679–83 (1986). Multivalent target binding proteins also have been made by covalently linking several single chain Fv molecules (scFv) to form a single polypeptide. See U.S. Pat. No. 5,892,020. A multivalent target binding protein which is basically an aggregate of scFv molecules has been disclosed in U.S. Pat. Nos. 6,025,165 and 5,837,242. A trivalent target binding protein comprising three scFv molecules has been described in Krott et al. *Protein Engineering* 10(4): 423–433 (1997).

A clearing agent may be used which is given between doses of the bsAb and the linker moiety. The present inventors have discovered that a clearing agent of novel mechanistic action may be used with the invention, namely a glycosylated anti-idiotypic Fab' fragment targeted against the disease targeting arm(s) of the bsAb. Anti-CEA (MN 14 Ab) x anti-peptide bsAb is given and allowed to accrete in disease targets to its maximum extent. To clear residual bsAb, an anti-idiotypic Ab to MN-14, termed WI2, is given, preferably as a glycosylated Fab' fragment. The clearing agent binds to the bsAb in a monovalent manner, while its appended glycosyl residues direct the entire complex to the liver, where rapid metabolism takes place. Then the therapeutic which is associated with the linker moiety is given to the subject. The WI2 Ab to the MN-14 arm of the bsAb has a high affinity and the clearance mechanism differs from other disclosed mechanisms (see Goodwin et al., *ibid*), as it does not involve cross-linking, because the WI2-Fab' is a monovalent moiety.

VI. Methods for Raising Antibodies

Abs to peptide backbones are generated by well-known methods for Ab production. For example, injection of an immunogen, such as (peptide)$_n$-KLH, wherein KLH is keyhole limpet hemocyanin, and n=1–30, in complete Freund's adjuvant, followed by two subsequent injections of the same immunogen suspended in incomplete Freund's adjuvant into immunocompetent animals, is followed three days after an i.v. boost of antigen, by spleen cell harvesting. Harvested spleen cells are then fused with Sp2/0-Ag14 myeloma cells and culture supernatants of the resulting clones analyzed for anti-peptide reactivity using a direct-binding ELISA. Fine specificity of generated Abs can be analyzed for by using peptide fragments of the original immunogen. These fragments can be prepared readily using an automated peptide synthesizer. For Ab production, enzyme-deficient hybridomas are isolated to enable selection of fused cell lines. This technique also can be used to raise antibodies to one or more of the chelates comprising the linker, e.g., In(III)-DTPA chelates. Monoclonal mouse antibodies to an In(III)-di-DTPA are known (Barbet '395 supra).

The antibodies used in the present invention are specific to a variety of cell surface or intracellular tumor-associated antigens as marker substances. These markers may be substances produced by the tumor or may be substances which accumulate at a tumor site, on tumor cell surfaces or within tumor cells, whether in the cytoplasm, the nucleus or in various organelles or sub-cellular structures. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcino embryonic antigen (CEA), which stimulate the production of antibodies having a greatly reduced cross-reactivity to non-tumor substances as disclosed in U.S. Pat. Nos. 4,361,644 and 4,444,744.

Another marker of interest is transmembrane activator and CAML-interactor (TACI). See Yu et al. *Nat. Immunol.* 1:252–256 (2000). Briefly, TACI is a marker for B-cell malignancies (e.g., lymphoma). Further it is known that TACI and B cell maturation antigen (BCMA) are bound by the tumor necrosis factor homolog a proliferation-inducing ligand (APRIL). APRIL stimulates in vitro proliferation of primary B and T cells and increases spleen weight due to accumulation of B cells in vivo. APRIL also competes with TALL-I (also called BLyS or BAFF) for receptor binding. Soluble BCMA and TACI specifically prevent binding of APRIL and block APRIL-stimulated proliferation of primary B cells. BCMA-Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T cell function.

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for producing humanized Mabs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference.

Alternatively, fully human antibodies can be obtained from transgenic non-human animals. See, e.g., Mendez et al., *Nature Genetics*, 15: 146–156 (1997); U.S. Pat. No. 5,633,425. For example, human antibodies can be recovered from transgenic mice possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., *Nature Genetics*, 16: 133 (1997). In this methodology microcells containing human chromosomes are fused with mouse embryonic stem cells. Transferred chromosomes are stably retained, and adult chimeras exhibit proper tissue-specific expression.

As an alternative, an antibody or antibody fragment of the present invention may be derived from human antibody fragments isolated from a combinatorial immunoglobulin library. See, e.g., Barbas et al., *METHODS: A Companion to Methods in Enzymology* 2: 119 (1991), and Winter et al., *Ann. Rev. Immunol.* 12: 433 (1994), which are incorporated by reference. Many of the difficulties associated with generating monoclonal antibodies by B-cell immortalization can be overcome by engineering and expressing antibody fragments in *E. coli*, using phage display. To ensure the recovery of high affinity, monoclonal antibodies a combinatorial immunoglobulin library must contain a large repertoire size. A typical strategy utilizes mRNA obtained from lymphocytes or spleen cells of immunized mice to synthesize cDNA using reverse transcriptase. The heavy- and light-chain genes are amplified separately by PCR and ligated into phage cloning vectors. Two different libraries are produced, one containing the heavy-chain genes and one containing the light-chain genes. Phage DNA is islolated from each library, and the heavy- and light-chain sequences are ligated together and packaged to form a combinatorial library. Each phage contains a random pair of heavy- and light-chain cDNAs and upon infection of *E. coli* directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from STRATAGENE Cloning Systems (La Jolla, Calif.).

A similar strategy can be employed to obtain high-affinity scFv. See, e.g., Vaughn et al., *Nat. Biotechnol.*, 14: 309–314 (1996). An scFv library with a large repertoire can be constructed by isolating V-genes from non-immunized human donors using PCR primers corresponding to all known $V_H$, $V_\kappa$ and $V_{80}$ gene families. Following amplification, the $V_\kappa$ and $V_\lambda$ pools are combined to form one pool. These fragments are ligated into a phagemid vector. The scFv linker, $(Gly_4, Ser)_3$, is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned using filters, as described above, or using inununotubes (Nunc; Maxisorp). Similar results can be achieved by constructing a combinatorial immunoglobulin library from lymphocytes or spleen cells of immunized rabbits and by expressing the scFv constructs in *P. pastoris*. See, e.g., Ridder et al., *Biotechnology*, 13: 255–260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., *Br. J. Cancer*, 78: 181–188 (1998); Osbourn et al., *Immunotechnology*, 2: 181–196 (1996).

Another form of an antibody fragment is a peptide coding for a single CDR. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2:106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166–179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137–185 (Wiley-Liss, Inc. 1995).

The bsAbs can be prepared by techniques known in the art, for example, an anti-CEA tumor Ab and an anti-peptide Ab are both separately digested with pepsin to their respective $F(ab')_2$s. The anti-CEA-Ab-$F(ab')_2$ is reduced with cysteine to generate Fab' monomeric units which are further reacted with the cross-linker bis(maleimido) hexane to produce Fab'-maleimide moieties. The anti-peptide Ab-$F(ab')_2$ is reduced with cysteine and the purified, recovered antipeptide Fab'-SH reacted with the anti-CEA-Fab'-maleimide to generate the Fab'×Fab' bi-specific Ab. Alternatively, the anti-peptide Fab'-SH fragment may be coupled with the anti-CEA F(ab')$_2$ to generate a F(ab')$_2$×Fab' construct, or with anti-CEA IgG to generate an IgG×Fab' bi-specific construct. In one embodiment, the IgG×Fab' construct can be prepared in a site-specific manner by attaching the antipeptide Fab' thiol group to anti-CEA IgG heavy-chain carbohydrate which has been periodate-oxidized, and subsequently activated by reaction with a commercially available hydrazide-maleimide cross-linker. The component Abs used can be chimerized or humanized by known techniques. A chimeric antibody is a recombinant protein that contains the variable domains and complementary determining regions derived from a rodent antibody, while the remainder of the antibody molecule is derived from a human antibody. Humanized antibodies are recombinant proteins in which murine complementarity determining regions of a monoclonal antibody have been transferred from heavy and light variable chains of the murine immunoglobulin into a human variable domain.

A variety of recombinant methods can be used to produce bi-specific antibodies and antibody fragments. For example, bi-specific antibodies and antibody fragments can be produced in the milk of transgenic livestock. See, e.g., Colman, A., Biochem. Soc. Symp., 63: 141–147, 1998; U.S. Pat. No. 5,827,690. Two DNA constructs are prepared which contain, respectively, DNA segments encoding paired immunoglobulin heavy and light chains. The fragments are cloned into expression vectors which contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

A chimeric Ab is constructed by ligating the cDNA fragment encoding the mouse light variable and heavy variable domains to fragment encoding the C domains from a human antibody. Because the C domains do not contribute to antigen binding, the chimeric antibody will retain the same antigen specificity as the original mouse Ab but will be closer to human antibodies in sequence. Chimeric Abs still contain some mouse sequences, however, and may still be immunogenic. A humanized Ab contains only those mouse amino acids necessary to recognize the antigen. This product is constructed by building into a human antibody framework the amino acids from mouse complementarity determining regions.

Other recent methods for producing bsAbs include engineered recombinant Abs which have additional cysteine residues so that they crosslink more strongly than the more common immunoglobulin isotypes. See, e.g., FitzGerald et al., Protein Eng. 10(10): 1221–1225, 1997. Another approach is to engineer recombinant fusion proteins linking two or more different single-chain antibody or antibody fragment segments with the needed dual specificities. See, e.g., Coloma et al., Nature Biotech. 15:159–163, 1997. A variety of bi-specific fusion proteins can be produced using molecular engineering. In one form, the bi-specific fusion protein is monovalent, consisting of, for example, a scFv with a single binding site for one antigen and a Fab fragment with a single binding site for a second antigen. In another form, the bi-specific fusion protein is divalent, consisting of, for example, an IgG with two binding sites for one antigen and two scFv with two binding sites for a second antigen.

Functional bi-specific single-chain antibodies (bscAb), also called diabodies, can be produced in mammalian cells using recombinant methods. See, e.g., Mack et al., Proc. Natl. Acad. Sci., 92: 7021–7025, 1995. For example, bscAb are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNA's obtained from each hybridoma are then joined to form a single-chain fragment in a two-step fusion PCR. The first PCR step introduces the $(Gly_4\text{-}Ser_1)_3$ (SEQ ID NO: 17) linker, and the second step joins the $V_L$ and $V_H$ amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into an eukaryotic expression vector. Functional protein expression can be obtained by transfecting the vector into chinese hamster ovary cells. Bi-specific fusion proteins are prepared in a similar manner. Bi-specific single-chain antibodies and bi-specific fusion proteins are included within the scope of the present invention.

Bi-specific fusion proteins linking two or more different single-chain antibodies or antibody fragments are produced in similar manner.

Large quantities of bscAb and fusion proteins can be produced using Escherichia coli expression systems. See, e.g., Zhenping et al., Biotechnology, 14: 192–196, 1996. A functional bscAb can be produced by the coexpression in E. coli of two "cross-over" scFv fragments in which the $V_L$ and $V_H$ domains for the two fragments are present on different polypeptide chains. The V light-chain ($V_L$) and V heavy-chain ($V_H$) domains of two antibodies of interest are isolated using standard PCR methods. The cDNA's are then ligated into a bacterial expression vector such that C-terminus of the $V_L$ domain of the first antibody of interest is ligated via a linker to the N-terminus of the $V_H$ domain of the second antibody. Similarly, the C-terminus of the $V_L$ domain of the second antibody of interest is ligated via a linker to the N-terminus of the $V_H$ domain of the first antibody. The resulting dicistronic operon is placed under transcriptional control of a strong promoter, e.g., the E. coli alkaline phosphatase promoter which is inducible by phosphate starvation. Alternatively, single-chain fusion constructs have successfully been expressed in E. coli using the lac promoter and a medium consisting of 2% glycine and 1% Triton X-100. See, e.g., Yang et al., Appl. Environ. Microbiol., 64: 2869–2874, 1998. An E. coli, heat-stable, enterotoxin II signal sequence is used to direct the peptides to the periplasmic space. After secretion, the two peptide chains associate to form a non-covalent heterodimer which possesses both antigen binding specificities. The bscAb is purified using standard procedures known in the art, e.g., Staphylococcal protein A chromatography.

Functional bscAb and fusion proteins also can be produced in the milk of transgenic livestock. See, e.g., Colman, A., *Biochem. Soc. Symp.*, 63: 141–147, 1998; U.S. Pat. No. 5,827,690. The bscAb fragment, obtained as described above, is cloned into an expression vector containing a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted bscAb is flanked on its 3' side by cognate genomic sequences from a mammary-specific gene. This provides a polyadenylation site and transcript-stabilizing sequences. The expression cassette is then injected into the pronuclei of fertilized, mammalian eggs, which are then implanted into the uterus of a recipient female and allowed to gestate. After birth, the progeny are screened for the presence of the introduced DNA by Southern analysis. Milk from transgenic females is analyzed for the presence and functionality of the bscAb using standard immunological methods known in the art. The bscAb can be purified from the milk using standard methods known in the art. Transgenic production of bscAb in milk provides an efficient method for obtaining large quantities of bscAb.

Functional bscAb and fusion proteins also can be produced in transgenic plants. See, e.g., Fiedler et al., *Biotech.*, 13: 1090–1093, 1995; Fiedler et al., *Immunotechnology*, 3: 205–216, 1997. Such production offers several advantages including low cost, large scale output and stable, long term storage. The bscAb fragment, obtained as described above, is cloned into an expression vector containing a promoter sequence and encoding a signal peptide sequence, to direct the protein to the endoplasmic recticulum. A variety of promoters can be utilized, allowing the practitioner to direct the expression product to particular locations within the plant. For example, ubiquitous expression in tobacco plants can be achieved by using the strong cauliflower mosaic virus 35S promoter, while organ specific expression is achieved via the seed specific legumin B4 promoter. The expression cassette is transformed according to standard methods known in the art. Transformation is verified by Southern analysis. Transgenic plants are analyzed for the presence and functionality of the bscAb using standard immunological methods known in the art. The bscAb can be purified from the plant tissues using standard methods known in the art.

Additionally, transgenic plants facilitate long term storage of bscAb and fusion proteins. Functionally active scFv proteins have been extracted from tobacco leaves after a week of storage at room temperature. Similarly, transgenic tobacco seeds stored for 1 year at room temperature show no loss of scFv protein or its antigen binding activity.

Functional bscAb and fusion proteins also can be produced in insect cells. See, e.g., Mahiouz et al., *J. Immunol. Methods*, 212: 149–160 (1998). Insect-based expression systems provide a means of producing large quantities of homogenous and properly folded bscAb. The baculovirus is a widely used expression vector for insect cells and has been successfully applied to recombinant antibody molecules. See, e.g., Miller, L. K., *Ann. Rev. Microbiol.*, 42: 177 (1988); Bei et al., *J. Immunol. Methods*, 186: 245 (1995). Alternatively, an inducible expression system can be utilized by generating a stable insect cell line containing the bscAb construct under the transcriptional control of an inducible promoter. See, e.g., Mahiouz et al., *J. Immunol. Methods*, 212: 149–160 (1998). The bscAb fragment, obtained as described above, is cloned into an expression vector containing the Drosphila metallothionein promoter and the human HLA-A2 leader sequence. The construct is then transfected into *D. melanogaster* SC-2 cells. Expression is induced by exposing the cells to elevated amounts of copper, zinc or cadmium. The presence and functionality of the bscAb is determined using standard immunological methods known in the art. Purified bscAb is obtained using standard methods known in the art.

Preferred bispecific antibodies of the instant invention are those which incorporate the Fv of MAb Mu9 and the Fv of MAb 679 or the Fv of MAb MN14 and the Fv of MAb 679, and their human, chimerized or humanized counterparts. The MN14, as well as its chimerized and humanized counterparts, are disclosed in U.S. Pat. No. 5,874,540. Also preferred are bispecific antibodies which incorporate one or more of the CDRs of Mu9 or 679. The antibody can also be a fusion protein or a bispecific antibody that incorporates a Class III anti-CEA antibody and the Fv of 679. Class III antibodies, including Class III anti-CEA are discussed in detail in U.S. Pat. No. 4,818,709.

VII. Other Applications

The present invention encompasses the use of the bsAb and a therapeutic agent associated with the linker moieties discussed above in intraoperative, intravascular, and endoscopic tumor and lesion detection, biopsy and therapy as described in U.S. Pat. No. 6,096,289.

The antibodies and antibody fragments of the present invention can be employed not only for therapeutic or imaging purposes, but also as aids in performing research in vitro. For example, the bsAbs of the present invention can be used in vitro to ascertain if a targetable construct can form a stable complex with one or more bsAbs. Such an assay would aid the skilled artisan in identifying targetable constructs which form stable complexes with bsAbs. This would, in turn, allow the skilled artisan to identify targetable constructs which are likely to be superior as therapeutic and/or imaging agents.

The assay is advantageously performed by combining the targetable construct in question with at least two molar equivalents of a bsAb. Following incubation, the mixture is analyzed by size-exclusion HPLC to determine whether or not the construct has bound to the bsAb. Alternatively, the assay is performed using standard combinatorial methods wherein solutions of various bsAbs are deposited in a standard 96 well plate. To each well, is added solutions of targetable construct(s). Following incubation and analysis, one can readily determine which construct(s) bind(s) best to which bsAb(s).

It should be understood that the order of addition of the bsAb to the targetable construct is not crucial; that is, the bsAb may be added to the construct and vice versa. Likewise, neither the bsAb nor the construct needs to be in solution; that is, they may be added either in solution or neat, whichever is most convenient. Lastly, the method of analysis for binding is not crucial as long as binding is established. Thus, one may analyze for binding using standard analytical methods including, but not limited to, FABMS, high-field NMR or other appropriate method in conjunction with, or in place of, size-exclusion HPLC.

VIII. EXAMPLES

A. Synthesis of Ac-Lys(HSG)-D-Tyr-Lys(HSG)-Lys(Tscg-Cys-)-NH$_2$ (IMP 243)

The peptide was synthesized as described by Karacay et. al. *Bioconjugate Chem.* 11:842–854 (2000) except D-tyrosine was used in place of the L-tyrosine and the N-trityl-HSG-OH was used in place of the DTPA. The final coupling of the N-trityl-HSG-OH was carried out using a ten fold excess of N-trityl-HSG-OH relative to the peptide on the resin. The N-trityl-HSG-OH (0.28 M in NMP) was activated using one equivalent (relative to HSG) of N-hydroxybenzotriazole, one equivalent of benzotrazole-1-yl-oxy-tris-(dimethylamino)phosphonium hexafluorophosphate (BOP) and two equivalents of diisopropylethylamine. The activated substrate was mixed with the resin for 15 hr at room temperature.

B. Tc-99m Kit Formulation Comprising IMP 243

A formulation buffer was prepared which contained 22.093 g hydroxypropyl-β-cyclodextrin, 0.45 g 2,4-dihydroxybenzoic acid, 0.257 g acetic acid sodium salt, and 10.889 g α-D-glucoheptonic acid sodium salt dissolved in 170 mL nitrogen degassed water. The solution was adjusted to pH 5.3 with a few drops of 1 M NaOH then further diluted to a total volume of 220 mL. A stannous buffer solution was prepared by diluting 0.2 mL of $SnCl_2$ (200 mg/mL) with 3.8 mL of the formulation buffer. The peptide Ac-Lys(HSG)-D-Tyr-Lys(HSG)-Lys(Tscg-Cys-)-$NH_2$ (0.0026 g), was dissolved in 78 mL of the buffer solution and mixed with 0.52 mL of the stannous buffer. The peptide solution was then filtered through a 0.22 ☐m Millex GV filter in 1.5 mL aliquots into 3 mL lyophilization vials. The filled vials were frozen immediately, lyophilized and crimp sealed under vacuum.

Pertechnetate solution (27 mCi) in 1.5 mL of saline was added to the kit. The kit was incubated at room temperature for 10 min and heated in a boiling water bath for 25 min. The kit was cooled to room temperature before use.

C. Peptides for Carrying Therapeutic/Imaging Radioisotopes to Tumors Via Bispecific Antibody Tumor Pretargeting DOTA-Phe-Lys(HSG)-Tyr-Lys(HSG)-$NH_2$ (SEQ ID NO: 15) (IMP 237) was synthesized to deliver therapeutic radioisotopes such as $^{99}Y$ or $^{177}Lu$ to tumors via bispecific antibody tumor pretargeting. The bispecific antibody is composed of one portion which binds to an antigen on the tumor and another portion which binds to the HSG peptide. The antibody which binds the HSG peptide is 679. This system can also be used to deliver imaging isotopes such as $^{111}In$-111.

Synthesis of IMP 237

IMP 237 was synthesized on Sieber Amide resin (Nova-Biochem) using standard Fmoc based solid phase peptide synthesis to assemble the peptide backbone with the following protected amino acids, in order: Fmoc-Lys(Aloc)-OH, Fmoc-Tyr(But)-OH, Fmoc-Lys(Aloc)-OH, Fmoc-Phe-OH, (Reagents from Advanced Chemtech) tri-t-butyl DOTA (Macrocyclics). The side lysine side chains were then deprotected with $Pd[P(Ph)_3]_4$ by the method of Dangles et.al. *J. Org. Chem.* 52:4984–4993 (1987). The HSG ligands were then added as Trityl HSG (synthesis described below) using the BOP/HBTU double coupling procedure used to attach the amino acids. The peptide was cleaved from the resin and the protecting groups were removed by treatment with TFA. The peptide was purified by HPLC to afford 0.6079 g of peptide from 1.823 g of Fmoc-Lys(Aloc)-Tyr(But)-Lys(Aloc)-NH-Sieber amide resin.

Synthesis of N-Trityl-HSG-OH

Glycine t-butyl ester hdyrochloride (15.263 g, $9.1\times10^{-2}$ mol) and 19.760 g $Na_2CO_3$ were mixed, then suspended in 50 mL $H_2O$ and cooled in an ice bath. Succinic anhydride (9.142 g, $9.14\times10^{-2}$ mol) was then added to the reaction solution which was allowed to warm slowly to room temperature and stir for 18 hr. Citric acid (39.911 g) was dissolved in 50 mL $H_2O$ and slowly added to the reaction solution and then extracted with 2×150 mL EtOAc. The organic extracts were dried over $Na_2SO_4$, filtered and concentrated to afford 25.709 g of a white solid.

The crude product (25.709 g) was dissolved in 125 mL dioxane, cooled in a room temperature water bath and mixed with 11.244 g of N-hydroxysuccinimide. Diisopropylcarbodiimide 15.0 mL was added to the reaction solution which was allowed to stir for one hour. Histamine dihydrochloride (18.402 g, $1.00\times10^{-1}$ mol) was then dissolved in 100 mL DMF and 35 mL diisopropylethylamine. The histamine mixture was added to the reaction solution which was stirred at room temperature for 21 hr. The reaction was quenched with 100 mL water and filtered to remove a precipitate. The solvents were removed under hi-vacuum on the rotary evaporator. The crude product was dissolved in 300 mL dichloromethane and extracted with 100 mL saturated $NaHCO_3$. The organic layer was dried over $Na_2SO_4$ and concentrated to afford 34.19 g of crude product as a yellow oil.

The crude product (34.19 g) was dissolved in 50 mL chloroform and mixed with 31 mL diisopropylethylamine. Triphenylmethyl chloride (25.415 g) was dissolved in 50 ml chloroform and added dropwise to the stirred reaction solution which was cooled in an ice bath. The reaction was stirred for 45 min and then quenched with 100 mL $H_2O$. The layers were separated and the organic solution was dried over $Na_2SO_4$ and concentrated to form a green gum. The gum was triturated with 100 mL $Et_2O$ to form a yellow precipitate which was washed with 3×50 mL portions of $Et_2O$. The solid was vacuum dried to afford 30.641 g (59.5% overall yield) of N-trityl-HSG-t-butyl ester.

N-trityl-HSG-t-butyl ester (20.620 g, $3.64\times10^{-2}$ mol) was dissolved in a solution of 30 mL chloroform and 35 mL glacial acetic acid. The reaction was cooled in an ice bath and 15 mL of $BF_3 \cdot Et_2O$ was slowly added to the reaction solution. The reaction was allowed to warm slowly to room temperature and mix for 5 hr. The reaction was quenched by pouring into 200 mL 1M NaOH and the product was extracted with 200 mL chloroform. The organic layer was dried over $Na_2SO_4$ and concentrated to afford a crude gum which was triturated with 100 mL $Et_2O$ to form a precipitate. The crude precipitate was poured into 400 mL 0.5 M pH 7.5 phosphate buffer and extracted with 2×200 mL EtOAc. The aqueous layer was acidified to pH 3.5 with 1 M HCl and extracted with 2×200 mL chloroform. A precipitate formed and was collected by filtration (8.58 g). The precipitate was the desired product by HPLC comparison to a previous sample (ESMS MH+511).

Radiolabeling $^{90}Y$ Kit Preparation

DOTA-Phe-Lys(HSG)-Tyr-Lys(HSG)-$NH_2$ (SEQ ID NO: 15) was dissolved in 0.25 M $NH_4OAc$/10% HPCD buffer at concentrations of 9, 18, 35,70 and 140 μg/mL. The solutions were sterile filtered through a 0.22 μm Millex GV filter in one mL aliquots into acid washed lyophilization vials. The filled vials were frozen immediately on filling and lyophilized. When the lyophilization cycle was complete the vials were sealed under vacuum and crimp sealed upon removal from the lyophilizer.

The $^{90}Y$ (400 μCi/kit) was diluted to 1 mL in deionized water and added to the lyophilized kits. The kits were heated in a boiling water bath for 15 min, the vials were cooled to room temperature and the labeled peptides were evaluated by reverse phase HPLC (HPLC conditions: Waters Nova-Pak C-18, 8×100 mm RCM column eluted at 3 mL/min with a linear gradient from 100% (0.1% TFA in $H_2O$) to 100% (90% $CH_3CN$, 0.1% TFA, 10% $H_2O$)). The HPLC analysis revealed that the minimum concentration of peptide needed for complete labeling, with this formulation, was 35 μg/mL. The reverse phase HPLC trace showed a sharp $^{90}Y$ labeled peptide peak. The labeled peptide was completely bound when mixed with excess 679 IgG by size exclusion HPLC.

Labeling with $^{111}$In

The $^{111}$In (~300 µCi/kit) was diluted to 0.5 mL in deionized water and added to the lyophilized kits. The kits were heated in a boiling water bath for 15 min, the vials were cooled and 0.5 mL of 2.56×10$^{-5}$ M In in 0.5 M acetate buffer was added and the kits were again heated in the boiling water bath for 15 min. The labeled peptide vials were cooled to room temperature and evaluated by reverse phase HPLC (HPLC conditions: Waters Nova-Pak C-18, 8×100 mm RCM column eluted at 3 mL/min with a linear gradient from 100% (0.1% TFA in H$_2$O) to 100% (90% CH$_3$CN, 0.1% TFA, 10% H$_2$O)). The HPLC analysis revealed that the minimum concentration of peptide needed for labeling (4.7% loose $^{111}$In), with this formulation, was 35 µg/mL. The reverse phase HPLC trace showed a sharp $^{111}$In labeled peptide peak. The labeled peptide was completely bound when mixed with excess 679 IgG by size exclusion HPLC.

In-Vivo Studies

Nude mice bearing GW-39 human colonic xenograft tumors (100–500 mg) were injected with the bispecific antibody hMN-14×m679 (1.5×10$^{-10}$ mol). The antibody was allowed to clear for 24 hr before the $^{111}$In labeled peptide (8.8 µCi, 1.5×10$^{-11}$ mol) was injected. The animals were sacrificed at 3, 24, 48 hr post injection.

The results of the biodistribution studies of the peptide in the mice pretargeted with hMN-14×m679 are shown in Table 1. The tumor to non-tumor ratios of the peptides in the pretargeting study are show in Table 2.

TABLE 1

Pretargeting With $^{111}$In Labeled Peptide 24 hr After Injection of hMN-14 x m679 % Injected/g Tissue

| Tissue | 3 hr After $^{111}$In IMP 237 | 24 hr After $^{111}$In IMP 237 | 48 hr After $^{111}$In IMP 237 |
|---|---|---|---|
| GW-39 | 7.25 ± 2.79 | 8.38 ± 1.70 | 5.39 ± 1.46 |
| Liver | 0.58 ± 0.13 | 0.62 ± 0.09 | 0.61 ± 0.16 |
| Spleen | 0.50 ± 0.14 | 0.71 ± 0.16 | 0.57 ± 0.15 |
| Kidney | 3.59 ± 0.75 | 2.24 ± 0.40 | 1.27 ± 0.33 |
| Lungs | 1.19 ± 0.26 | 0.44 ± 0.10 | 0.22 ± 0.06 |
| Blood | 2.42 ± 0.61 | 0.73 ± 0.17 | 0.17 ± 0.06 |
| Stomach | 0.18 ± 0.03 | 0.09 ± 0.02 | 0.07 ± 0.02 |
| Sm. Int. | 0.65 ± 0.74 | 0.18 ± 0.03 | 0.11 ± 0.02 |
| Lg. Int. | 0.30 ± 0.07 | 0.17 ± 0.03 | 0.13 ± 0.03 |

TABLE 2

Pretargeting With $^{111}$In Labeled Peptides 24 hr After Injection of hMN-14 x m679 Tumor/Non-Tumor Tissue Ratios

| Tissue | 3 hr After $^{111}$In IMP 237 | 24 hr After $^{111}$In IMP 237 | 48 hr After $^{111}$In IMP 237 |
|---|---|---|---|
| Liver | 12.6 ± 4.44 | 13.6 ± 2.83 | 8.88 ± 1.78 |
| Spleen | 15.1 ± 6.32 | 12.1 ± 2.86 | 9.50 ± 1.62 |
| Kidney | 2.04 ± 0.74 | 3.84 ± 1.04 | 4.25 ± 0.19 |
| Lungs | 6.11 ± 1.96 | 19.6 ± 5.91 | 25.4 ± 6.00 |
| Blood | 3.04 ± 1.13 | 11.9 ± 3.20 | 31.9 ± 4.79 |
| Stomach | 40.5 ± 16.5 | 104. ± 39.6 | 83.3 ± 16.5 |
| Sm. Int. | 18.9 ± 12.6 | 47.5 ± 10.3 | 49.5 ± 7.83 |
| Lg. Int. | 25.2 ± 10.6 | 50.1 ± 16.7 | 43.7 ± 9.35 |

Serum Stability of DOTA-Phe-Lys(HSG)-Tyr-Lys(HSG)-NH2 (SEQ ID NO: 15) (IMP 237) and DOTA-Phe-Lys(HSG)-D-Tyr-Lys(HSG)-NH2 (IMP 241)

Peptide Labeling and HPLC Analysis

The peptides, IMP 237 and IMP 241, were labeled according to the procedure described by Karacay et. al. *Bioconjugate Chem.* 11:842–854 (2000). The peptide, IMP 241 (0.0019 g), was dissolved in 587 µl 0.5 M NH$_4$Cl, pH 5.5. A 1.7 µL aliquot of the peptide solution was diluted with 165 µl 0.5 M NH$_4$Cl, pH 5.5. The $^{111}$In (1.8 mCi) in 10 µL was added to the peptide solution and the mixture was heated in a boiling water bath for 30 min.

The labeled peptide was analyzed by HPLC using a Waters 8×100 mm radial-pak, nova-pak C-18 RCM cartridge column. The column was eluted at 3 mL/min with a linear gradient which started with 100% of 0.1% TFA in water and went to 100% of 0.1% TFA in 90% acetonitrile and 10% water over 10 min. There was about 6% loose $^{111}$In in this labeling which came out at the void volume of the column (1.6 min). There were also some $^{111}$In labeled peaks at 5 min and 6.6 to 8 min. The $^{111}$In labeled peptide was eluted at 8.8 min as a single peak. The HPLC profile of $^{111}$In IMP 237 was nearly identical to $^{111}$In IMP 241.

Serum Stability

An aliquot (30 µL) of $^{111}$In IMP 241 was placed in 300 µL of fresh mouse serum and placed in a 37° C. incubator. The peptide was monitored as described above by HPLC. An aliquot (24 µL) of $^{111}$In IMP 237 was placed in 230 µL of fresh mouse serum and placed in a 37° C. incubator. The peptide was monitored as described above by HPLC. The analysis showed that the $^{111}$In IMP 241 may have decomposed slightly (~5%) after heating 22 hr in mouse serum at 37° C. The $^{111}$In IMP 237 was about 70% converted to the shorter retention time peak after incubation for 22 hr at 37° C.

Conclusion

The D-tyrosine in the IMP 241 peptide slows the decomposition of the peptide in mouse serum compared to IMP 237.

In Vivo Stability of IMP 237 and IMP 241 Compared

The in vivo stabilities of $^{111}$In IMP 237 and $^{111}$In IMP 241 were compared by examining (by HPLC) urine samples from mice at 30 and 60 min. The peptides, IMP 241 and IMP 237, were $^{111}$In-111 labeled as described above.

The labeled peptides were injected into Balb/c mice which were sacrificed at 30 min and 60 min post injection of the peptides using one mouse per time point. The attached HPLC traces indicate that $^{111}$In IMP 241 was excreted intact while $^{111}$In IMP 237 was almost completely metabolized to a new $^{111}$In labeled peptide.

Conclusion

The replacement of Tyr with D-Tyr in the peptide backbone minimized metabolism of the peptide in-vivo.

Additional In Vivo Studies

Nude mice bearing GW-39 human colonic xenograft tumors (100–500 mg) were injected with the bispecific antibody mMu9×m679 (1.5×10$^{-10}$ mol). The antibody was allowed to clear for 48 hr before the $^{111}$In labeled peptides (8.8 µCi, 1.5×10$^{-11}$ mol) were injected. The animals were sacrificed at 3, 24, 48 hr post injection.

The results of the biodistribution studies of the peptides in the mice pretargeted with mMU9×m679 are shown in Table 3. The tumor to non-tumor ratios of the peptides in the pretargeting study are show in Table 4. The data in Table 5 shows the biodistribution of the peptides in mice that were not pretreated with the bispecific antibody.

TABLE 3

Pretargeting With $^{111}$In Labeled Peptides 48 hr After Injection of mMU9 x m679
% Injected/g Tissue

| Tissue | 3 hr After $^{111}$In Peptide | | 24 hr After $^{111}$In Peptide | | 48 hr After $^{111}$In Peptide | |
|---|---|---|---|---|---|---|
|  | IMP 237 | IMP 241 | IMP 237 | IMP 241 | IMP 237 | IMP 241 |
| GW-39 | 18.3 ± 7.17 | 26.7 ± 14.1 | 16.7 ± 8.22 | 14.8 ± 4.56 | 12.9 ± 1.10 | 12.3 ± 2.11 |
| Liver | 0.41 ± 0.10 | 0.66 ± 0.34 | 0.32 ± 0.08 | 0.32 ± 0.09 | 0.28 ± 0.09 | 0.32 ± 0.21 |
| Spleen | 0.34 ± 0.12 | 0.63 ± 0.38 | 0.34 ± 0.12 | 0.25 ± 0.07 | 0.28 ± 0.07 | 0.31 ± 0.22 |
| Kidney | 3.62 ± 0.71 | 4.28 ± 0.77 | 2.51 ± 0.54 | 2.34 ± 0.70 | 1.78 ± 0.38 | 1.17 ± 0.43 |
| Lungs | 0.61 ± 0.15 | 1.03 ± 0.65 | 0.22 ± 0.07 | 0.21 ± 0.07 | 0.12 ± 0.04 | 0.14 ± 0.08 |
| Blood | 1.16 ± 0.48 | 1.78 ± 1.49 | 0.21 ± 0.13 | 0.15 ± 0.05 | 0.08 ± 0.03 | 0.10 ± 0.09 |
| Stomach | 0.12 ± 0.04 | 0.21 ± 0.09 | 0.05 ± 0.01 | 0.05 ± 0.02 | 0.04 ± 0.01 | 0.03 ± 0.02 |
| Sm. Int. | 0.23 ± 0.04 | 0.50 ± 0.27 | 0.12 ± 0.02 | 0.09 ± 0.06 | 0.11 ± 0.08 | 0.07 ± 0.06 |
| Lg. Int. | 0.34 ± 0.16 | 0.38 ± 0.15 | 0.15 ± 0.07 | 0.10 ± 0.02 | 0.12 ± 0.07 | 0.09 ± 0.05 |

TABLE 4

Pretargeting With $^{111}$In Labeled Peptides 48 hr After Injection of mMU9 x m679
Tumor/Non-Tumor Tissue Ratios

| Tissue | 3 hr After $^{111}$In Peptide | | 24 hr After $^{111}$In Peptide | | 48 hr After $^{111}$In Peptide | |
|---|---|---|---|---|---|---|
|  | IMP 237 | IMP 241 | IMP 237 | IMP 241 | IMP 237 | IMP 241 |
| Liver | 45.6 ± 17.8 | 41.8 ± 19.6 | 49.8 ± 16.6 | 47.1 ± 8.68 | 49.1 ± 13.6 | 45.1 ± 13.9 |
| Spleen | 56.8 ± 23.8 | 43.5 ± 9.77 | 47.4 ± 14.7 | 59.6 ± 13.0 | 47.5 ± 10.6 | 50.2 ± 19.0 |
| Kidney | 5.13 ± 2.18 | 6.05 ± 2.41 | 6.43 ± 2.24 | 6.58 ± 2.42 | 7.43 ± 1.02 | 11.2 ± 2.61 |
| Lungs | 30.5 ± 10.6 | 28.4 ± 12.8 | 76.4 ± 34.1 | 72.7 ± 21.9 | 115. ± 36.6 | 102. ± 37.1 |
| Blood | 18.6 ± 12.0 | 19.0 ± 11.8 | 86.9 ± 36.2 | 108. ± 41.0 | 187. ± 76.3 | 181. ± 86.6 |
| Stomach | 156. ± 86.1 | 126. ± 49.6 | 303. ± 95.9 | 328. ± 96.7 | 344. ± 101. | 456. ± 193. |
| Sm. Int. | 80.7 ± 29.0 | 59.0 ± 31.0 | 143. ± 60.7 | 193. ± 83.7 | 153. ± 67.7 | 217. ± 73.5 |
| Lg. Int. | 56.3 ± 19.7 | 78.6 ± 54.4 | 116. ± 36.9 | 155. ± 42.4 | 133. ± 47.6 | 153. ± 43.1 |

TABLE 5

Biodistribution of $^{111}$In Labeled Peptides Alone

| Tissue | 30 min After $^{111}$In Peptide | | 3 hr After $^{111}$In Peptide | | 24 hr After $^{111}$In Peptide | |
|---|---|---|---|---|---|---|
|  | IMP 237 | IMP 241 | IMP 237 | IMP 241 | IMP 237 | IMP 241 |
| GW-39 | 2.99 ± 1.11 | 2.73 ± 0.37 | 0.17 ± 0.05 | 0.31 ± 0.12 | 0.11 ± 0.02 | 0.11 ± 0.08 |
| Liver | 0.48 ± 0.06 | 0.50 ± 0.09 | 0.15 ± 0.02 | 1.07 ± 1.61 | 0.15 ± 0.01 | 0.09 ± 0.04 |
| Spleen | 0.42 ± 0.08 | 0.43 ± 0.22 | 0.09 ± 0.04 | 0.13 ± 0.05 | 0.13 ± 0.02 | 0.08 ± 0.03 |
| Kidney | 5.85 ± 0.37 | 7.31 ± 0.53 | 3.55 ± 0.44 | 3.21 ± 0.45 | 2.18 ± 0.24 | 2.61 ± 0.51 |
| Lungs | 1.26 ± 0.24 | 1.12 ± 0.26 | 0.13 ± 0.02 | 0.15 ± 0.06 | 0.06 ± 0.00 | 0.07 ± 0.06 |
| Blood | 1.62 ± 0.34 | 1.59 ± 0.29 | 0.12 ± 0.02 | 0.02 ± 0.01 | 0.03 ± 0.01 | 0.00 ± 0.00 |
| Stomach | 0.59 ± 0.32 | 0.52 ± 0.16 | 0.04 ± 0.01 | 0.07 ± 0.03 | 0.03 ± 0.01 | 0.04 ± 0.04 |
| Sm. Int. | 0.55 ± 0.13 | 2.52 ± 3.73 | 0.09 ± 0.01 | 0.17 ± 0.08 | 0.08 ± 0.01 | 0.04 ± 0.01 |
| Lg. Int. | 0.33 ± 0.05 | 0.30 ± 0.07 | 0.33 ± 0.15 | 0.32 ± 0.14 | 0.05 ± 0.01 | 0.07 ± 0.03 |

IX. References

All references cited herein are hereby incorporated herein by reference in their entireties.

Additional references of interest include the following:

Bamias, A., and Epenetos, A. A. Two-step strategies for the diagnosis and treatment of cancer with bioconjugates. *Antibody, Immunoconjugates, Radiopharm.* 1992; 5: 385–395.

Barbet, J., Peltier, P., Bardet, S., Vuillez, J P., Bachelot, I., Denet, S., Olivier, P., Lecia, F., Corcuff, B., Huglo, D., Proye, C., Rouvier, E., Meyer, P., Chatal, J. F. Radioimmunodetection of medullary thyroid carcinoma using indium-111 bivalent hapten and anti-CEAxanti-DTPA-indium bispecifc antibody. *J. Nucl. Med.* 1998; 39:1172–1178.

Bos, E S., Kuijpers, W H A., Meesters-Winters, M., Pham, D T., deHaan, A S., van Doormalen, Am., Kasperson, F. M., vanBoeckel, C A A and Gouegeon-Bertrand, F. In vitro evaluation of DNA-DNA hybridization as a two-step approach in radioimmunotherapy of cancer. *Cancer Res.* 1994; 54:3479–3486.

Carr et al., WO00/34317.

Gautherot, E., Bouhou, J., LeDoussal, J-M., Manetti, C., Martin, M., Rouvier, E., Barbet, J. Therapy for colon carcinoma xenografts with bi-specific antibody-targeted, iodine-131-labeled bivalent hapten. *Cancer* suppl. 1997; 80: 2618–2623.

Gautherot, E., Bouhou, J., Loucif, E., Manetti, C., Martin, M., LeDoussal, J. M., Rouvier, E., Barbet, J. Radioimmunotherapy of LS174T colon carcinoma in nude mice using an iodine-131-labeled bivalent hapten combined with an anti-CEA×anti-indium-DTPA bi-specific antibody. *J. Nucl. Med.* Suppl. 1997; 38: 7p.

Goodwin, D. A., Meares, C F., McCall, M J., McTigue, M., Chaovapong, W. Pre-targeted immunoscintigraphy of murine tumors with indium-111-labeled bifunctional haptens. *J. Nucl. Med.* 1988; 29:226–234.

Greenwood, F. C. and Hunter, W. M. The preparation of I-131 labeled human growth hormone of high specific radioactivity. *Biochem.* 1963; 89:114–123.

Hawkins, G. A., McCabe, R. P., Kim, C.-H., Subramanian, R., Bredehorst, R., McCullers, G. A., Vogel, C.-W., Hanna, M. G. Jr., and Pomata, N. Delivery of radionuclides to pretargeted monoclonal antibodies using dihydrofolate reductase and methotrexate in an affinity system. *Cancer Res.* 1993; 53: 2368–2373.

Kranenborg, M. h., Boerman, O. C., Oosterwijk-Wakka, j., weijert, M., Corstens, F., Oosterwijk, E. Development and characterization of anti-renal cell carcinoma×antichelate bi-specific monoclonal antibodies for two-phase targeting of renal cell carcinoma. *Cancer Res.*(suppl) 1995; 55: 5864s–5867s.

Losman M. J., Qu Z., Krishnan I. S., Wang J., Hansen H. J., Goldenberg D. M., Leung S. O. *Clin. Cancer Res.* 1999; 5(10 Suppl.):3101s–3105s.

Penefsky, H. S. A centrifuged column procedure for the measurement of ligand binding by beef heart F1. Part G. *Methods Enzymol.* 1979; 56:527–530.

Schuhmacher, J., Klivenyi, G., Matys, R., Stadler, M., Regiert, T., Hauser, H., Doll, J., Maier-Borst, W., Zoller, M. Multistep tumor targeting in nude mice using bi-specific antibodies and a gallium chelate suitable for immunocintigraphy with positron emission tomography. *Cancer Res.* 1995; 55, 115–123.

Sharkey, R M., Karacay, Griffiths, G L., Behr, T M., Blumenthal, R D., Mattes, M J., Hansen, H J., Goldenberg. Development of a streptavidin-anti-carcinoembryonic ntigen antibody, radiolabeled biotin pretargeting method for radioimmunotherapy of colorectal cancer. Studies in a human colon cancer xenograft model. *Bioconjugate Chem* 1997; 8:595–604.

Stickney, D R., Anderson, L D., Slater, J B., Ahlem, C N., Kirk, G A., Schweighardt, S A and Frincke, J M. Bifunctional antibody: a binary radiopharmaceutical delivery system for imaging colorectal carcinoma. *Cancer Res.* 1991;51: 6650–6655.

What is claimed is:

1. A method of treating or identifying diseased tissues in a subject, comprising:
   (A) administering to said subject a bi-specific antibody or antibody fragment having at least one arm that specifically binds a targeted tissue and at least one other arm that specifically binds a targetable conjugate comprising at least two HSG haptens,
   wherein said at least one other arm that specifically binds a targetable conjugate comprising at least two HSG haptens comprises the Fv of mAb 679;
   (B) optionally, administering to said subject a clearing composition, and allowing said composition to clear non-localized antibodies or antibody fragments from circulation;
   (C) administering to said subject a targetable conjugate which comprises a carrier portion which comprises or bears at least two HSG haptens and may comprise a diagnostic or therapeutic cation, and/or one or more chelated or chemically bound therapeutic or diagnostic agents, or enzymes; and
   (D) when said targetable conjugate comprises an enzyme, further administering to said subject
      1) a prodrug, when said enzyme is capable of converting said prodrug to a drug at the target site; or
      2) a drug which is capable of being detoxified in said subject to form an intermediate of lower toxicity, when said enzyme is capable of reconverting said detoxified intermediate to a toxic form, and, therefore, of increasing the toxicity of said drug at the target site, or
      3) a prodrug which is activated in said subject through natural processes and is subject to detoxification by conversion to an intermediate of lower toxicity, when said enzyme is capable of reconverting said detoxified intermediate to a toxic form, and, therefore, of increasing the toxicity of said drug at the target site.

2. The method of claim 1, wherein said diagnostic agent emits 25–600 keV gamma particles and/or positrons.

3. The method of claim 2, wherein said diagnostic agent is selected from the group consisting of $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, $^{123}$I, $^{124}$I, $^{125}$I, and $^{131}$I.

4. The method of claim 1, wherein said therapeutic agent is a drug, prodrug or toxin.

5. The method of claim 4, wherein said prod rug is selected from the group consisting of epirubicin glucuronide, CPT-11, etoposide glucuronide, daunomicin glucuronide and doxorubicin glucuronide.

6. The method of claim 4, wherein said toxin is selected from the group consisting of ricin, abrin, ribonuclease, DNase I, *Staphylococcal* enterotoxin-A, pokeweed antiviral protein, gelonin, diphtherin toxin, *Pseudomonas* exotoxin, and *Pseudomonas* endotoxin.

7. The method of claim 1, wherein said targetable conjugate further comprises a therapeutic nuclide bound thereto.

8. The method of claim 7, wherein said therapeutic nuclide is selected from the group consisting of $^{32}$P, $^{33}$P, $^{47}$Sc, $^{64}$Cu, $^{67}$Cu, $^{67}$Ga, $^{90}$Y, $^{111}$Ag, $^{111}$In, $^{125}$I, $^{131}$I, $^{142}$Pr, $^{153}$Sm, $^{161}$Tb, $^{166}$Dy, $^{166}$Ho, $^{177}$Lu, $^{186}$Re, $^{188}$Re, $^{189}$Re, $^{212}$Pb, $^{212}$Bi, $^{213}$Bi, $^{211}$At, $^{223}$Ra and $^{225}$Ac.

9. The method of claim 1, wherein said targetable conjugate comprises one or more radioactive isotopes useful for killing diseased tissue.

10. The method of claim 1, wherein said targetable conjugate comprises $^{10}$B atoms, and said method further comprises the step of irradiating said boron atoms localized at said diseased tissue, thereby effecting BNCT of said diseased tissue.

11. The method of claim 1, wherein said targetable conjugate comprises one or more image enhancing agents for use in magnetic resonance imaging (MRI).

12. The method of claim 11, wherein said enhancing agent is selected from the group consisting of Mn, Fe and Gd.

13. The method of claim 1, wherein the targetable conjugate comprises one or more agents for photodynamic therapy.

14. The method of claim 13, wherein said agent for photodynamic therapy is a photosensitizer.

15. The method of claim 14, wherein said photosensitizer is selected from the group consisting of benzoporphyrin monoacid ring A (BPD-MA), tin etiopurpurin (SnET2), sulfonated aluminum phthalocyanine (AISPc) and lutetium texaphyrin (Lutex).

16. The method of claim 1, wherein said at least one arm that specifically binds a targeted tissue is a monoclonal antibody or a fragment of a monoclonal antibody.

17. The method of claim 1, wherein said targetable conjugate comprises doxorubicin, SN-38, etoposide, methotrexate, 6-mercaptopurine or etoposide phosphate.

18. The method of claim 1, wherein said targeted tissue is a tumor.

19. The method of claim 18, wherein said tumor produces or is associated with colon-specific antigen-p (CSAp).

20. The method of claim 19, wherein said at least one arm of the bispecific antibody that specifically binds a targeted tissue comprises one or more of the CDRs of Mu-9.

21. The method of claim 20, wherein said bispecific antibody is humanized.

22. The method of claim 20, wherein the bispecific antibody comprises the Fv of mAb Mu-9.

23. The method of claim 18, wherein the bispecific antibody is a fusion protein.

24. The method of claim 18, wherein the tumor produces carcinoembryonic antigen (CEA).

25. The method of claim 24, wherein said at least one arm of the bispecific antibody that specifically binds a targeted tissue comprises one or more of the CDRs of MN-14.

26. The method of claim 25, wherein said bispecific antibody is humanized.

27. The method of claim 25, wherein the bispecific antibody comprises the Fv of mAb MN-14.

28. The method of claim 25, wherein the bispecific antibody is a fusion protein.

29. The method of claim 28, wherein the fusion protein is trivalent, and incorporates the Fv of an antibody reactive with CSAp.

30. The method of claim 24, wherein the bispecific antibody incorporates a Class III anti-CEA antibody.

* * * * *

SEQUENCE LISTING

<160> NUMBER OF SEQ ID NOS: 18

<210> SEQ ID NO 1
<211> LENGTH: 339
<212> TYPE: DNA
<213> ORGANISM: Artificial Sequence
<220> FEATURE:
<221> NAME/KEY: CDS
<222> LOCATION: (1)..(339)
<220> FEATURE:
<223> OTHER INFORMATION: Description of Artificial Sequence: Synthetic
      679 Vk nucleotide sequence

<400> SEQUENCE: 1

```
gac att gtg atg tca caa tct cca tcc tcc ctg gct gtg tca cca gga        48
Asp Ile Val Met Ser Gln Ser Pro Ser Ser Leu Ala Val Ser Pro Gly
 1               5                  10                  15 gag aag gtc act atg acc tgc aaa tcc agt cag agt ctg ttc aac agt        96
Glu Lys Val Thr Met Thr Cys Lys Ser Ser Gln Ser Leu Phe Asn Ser
             20                  25                  30 aga acc cga aag aac tac ttg ggt tgg tac cag cag aaa cca ggg cag       144
Arg Thr Arg Lys Asn Tyr Leu Gly Trp Tyr Gln Gln Lys Pro Gly Gln
         35                  40                  45 tct cct aaa ctt ctg atc tac tgg gca tct act cgg gaa tct ggg gtc       192
Ser Pro Lys Leu Leu Ile Tyr Trp Ala Ser Thr Arg Glu Ser Gly Val
     50                  55                  60 cct gat cgc ttc aca ggc agt gga tct ggg aca gat ttc act ctc acc       240
Pro Asp Arg Phe Thr Gly Ser Gly Ser Gly Thr Asp Phe Thr Leu Thr
 65                  70                  75                  80 atc aac agt gtg cag tct gaa gac ctg gca gtt tat tac tgc act caa       288
Ile Asn Ser Val Gln Ser Glu Asp Leu Ala Val Tyr Tyr Cys Thr Gln
                 85                  90                  95 gtt tat tat ctg tgc acg ttc ggt gct ggg acc aag ctg gag ctg aaa       336
Val Tyr Tyr Leu Cys Thr Phe Gly Ala Gly Thr Lys Leu Glu Leu Lys
            100                 105                 110 cgg                                                                   339
Arg
```

```
<210> SEQ ID NO 2
<211> LENGTH: 113
<212> TYPE: PRT
<213> ORGANISM: Artificial Sequence
<220> FEATURE:
<223> OTHER INFORMATION: Description of Artificial Sequence: Synthetic
      679 Vk amino acid sequence

<400> SEQUENCE: 2

Asp Ile Val Met Ser Gln Ser Pro Ser Ser Leu Ala Val Ser Pro Gly
 1               5                  10                  15

Glu Lys Val Thr Met Thr Cys Lys Ser Gln Ser Leu Phe Asn Ser
            20                  25                  30

Arg Thr Arg Lys Asn Tyr Leu Gly Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Asn Ser Val Gln Ser Glu Asp Leu Ala Val Tyr Tyr Cys Thr Gln
                85                  90                  95

Val Tyr Tyr Leu Cys Thr Phe Gly Ala Gly Thr Lys Leu Glu Leu Lys
            100                 105                 110

Arg

<210> SEQ ID NO 3
<211> LENGTH: 354
<212> TYPE: DNA
<213> ORGANISM: Artificial Sequence
<220> FEATURE:
<221> NAME/KEY: CDS
<222> LOCATION: (1)..(354)
<220> FEATURE:
<223> OTHER INFORMATION: Description of Artificial Sequence: Synthetic
      679 Vh nucleotide sequence

<400> SEQUENCE: 3 gtc caa ctg cag gag tca ggg gga gac tta gtg aag cct gga ggg tcc        48
Val Gln Leu Gln Glu Ser Gly Gly Asp Leu Val Lys Pro Gly Gly Ser
 1               5                  10                  15 ctg aaa ctc tcc tgt gca gcc tct gga ttc act ttc agt att tac acc        96
Leu Lys Leu Ser Cys Ala Ala Ser Gly Phe Thr Phe Ser Ile Tyr Thr
            20                  25                  30 atg tct tgg ctt cgc cag act ccg gaa aag agg ctg gag tgg gtc gca       144
Met Ser Trp Leu Arg Gln Thr Pro Glu Lys Arg Leu Glu Trp Val Ala
        35                  40                  45 acc ctg agt ggt gat ggt gat gac atc tac tat cca gac agt gtg aag       192
Thr Leu Ser Gly Asp Gly Asp Asp Ile Tyr Tyr Pro Asp Ser Val Lys
    50                  55                  60 ggt cga ttc acc atc tcc aga gac aat gcc aag aac aac cta tat ctg       240
Gly Arg Phe Thr Ile Ser Arg Asp Asn Ala Lys Asn Asn Leu Tyr Leu
65                  70                  75                  80 caa atg aac agt cta agg tct gcg gac acg gcc ttg tat tac tgt gca       288
Gln Met Asn Ser Leu Arg Ser Ala Asp Thr Ala Leu Tyr Tyr Cys Ala
                85                  90                  95 agg gtg cga ctt ggg gac tgg gac ttc gat gtc tgg ggc cca ggg acc       336
Arg Val Arg Leu Gly Asp Trp Asp Phe Asp Val Trp Gly Pro Gly Thr
            100                 105                 110 acg gtc tcc gtc tcc tca                                                354
Thr Val Ser Val Ser Ser
        115
```

-continued

<210> SEQ ID NO 4
<211> LENGTH: 118
<212> TYPE: PRT
<213> ORGANISM: Artificial Sequence
<220> FEATURE:
<223> OTHER INFORMATION: Description of Artificial Sequence: Synthetic
      679 Vh amino acid sequence

<400> SEQUENCE: 4

```
Val Gln Leu Gln Glu Ser Gly Gly Asp Leu Val Lys Pro Gly Gly Ser
 1               5                  10                  15

Leu Lys Leu Ser Cys Ala Ala Ser Gly Phe Thr Phe Ser Ile Tyr Thr
            20                  25                  30

Met Ser Trp Leu Arg Gln Thr Pro Glu Lys Arg Leu Glu Trp Val Ala
        35                  40                  45

Thr Leu Ser Gly Asp Gly Asp Ile Tyr Tyr Pro Asp Ser Val Lys
 50                  55                  60

Gly Arg Phe Thr Ile Ser Arg Asp Asn Ala Lys Asn Asn Leu Tyr Leu
 65                  70                  75                  80

Gln Met Asn Ser Leu Arg Ser Ala Asp Thr Ala Leu Tyr Tyr Cys Ala
            85                  90                  95

Arg Val Arg Leu Gly Asp Trp Asp Phe Asp Val Trp Gly Pro Gly Thr
           100                 105                 110

Thr Val Ser Val Ser Ser
           115
```

<210> SEQ ID NO 5
<211> LENGTH: 741
<212> TYPE: DNA
<213> ORGANISM: Artificial Sequence
<220> FEATURE:
<221> NAME/KEY: CDS
<222> LOCATION: (1)..(741)
<220> FEATURE:
<223> OTHER INFORMATION: Description of Artificial Sequence: Synthetic
      scFv of Mab 679

<400> SEQUENCE: 5

```
gac att gtg atg tca caa tct cca tcc tcc ctg gct gtg tca cca gga      48
Asp Ile Val Met Ser Gln Ser Pro Ser Ser Leu Ala Val Ser Pro Gly
 1               5                  10                  15 gag aag gtc act atg acc tgc aaa tcc agt cag agt ctg ttc aac agt      96
Glu Lys Val Thr Met Thr Cys Lys Ser Ser Gln Ser Leu Phe Asn Ser
            20                  25                  30 aga acc cga aag aac tac ttg ggt tgg tac cag cag aaa cca ggg cag     144
Arg Thr Arg Lys Asn Tyr Leu Gly Trp Tyr Gln Gln Lys Pro Gly Gln
        35                  40                  45 tct cct aaa ctt ctg atc tac tgg gca tct act cgg gaa tct ggg gtc     192
Ser Pro Lys Leu Leu Ile Tyr Trp Ala Ser Thr Arg Glu Ser Gly Val
 50                  55                  60 cct gat cgc ttc aca ggc agt gga tct ggg aca gat ttc act ctc acc     240
Pro Asp Arg Phe Thr Gly Ser Gly Ser Gly Thr Asp Phe Thr Leu Thr
 65                  70                  75                  80 atc aac agt gtg cag tct gaa gac ctg gca gga ggc tcc gga ggc ggt     288
Ile Asn Ser Val Gln Ser Glu Asp Leu Ala Gly Gly Ser Gly Gly Gly
            85                  90                  95 ggg agt gag gtg cag ctg cag gag tct ggg gga gac tta gtg aag cct     336
Gly Ser Glu Val Gln Leu Gln Glu Ser Gly Gly Asp Leu Val Lys Pro
           100                 105                 110 gga ggg tcc ctg aaa ctc tcc tgt gca gcc tct gga ttc act ttc agt     384
Gly Gly Ser Leu Lys Leu Ser Cys Ala Ala Ser Gly Phe Thr Phe Ser
```

```
                115                 120                 125
att tac acc atg tct tgg ctt cgc cag act ccg gaa aag agg ctg gag    432
Ile Tyr Thr Met Ser Trp Leu Arg Gln Thr Pro Glu Lys Arg Leu Glu
    130                 135                 140 tgg gtc gca acc ctg agt gtt tat tac tgc act caa gtt tat tat ctg    480
Trp Val Ala Thr Leu Ser Val Tyr Tyr Cys Thr Gln Val Tyr Tyr Leu
145                 150                 155                 160 tgc acg ttc ggt gct ggg acc aag ctg gag ctg aaa cga gga ggt ggc    528
Cys Thr Phe Gly Ala Gly Thr Lys Leu Glu Leu Lys Arg Gly Gly Gly
                165                 170                 175 gga tca gga ggc ggt gat ggt gat gac atc tac tat cca gac agt gtg    576
Gly Ser Gly Gly Gly Asp Gly Asp Asp Ile Tyr Tyr Pro Asp Ser Val
            180                 185                 190 aag ggt cga ttc acc atc tcc aga gac aat gcc aag aac aac cta tat    624
Lys Gly Arg Phe Thr Ile Ser Arg Asp Asn Ala Lys Asn Asn Leu Tyr
        195                 200                 205 ctg caa atg aac agt cta agg tct gcg gac acg gcc ttg tat tac tgt    672
Leu Gln Met Asn Ser Leu Arg Ser Ala Asp Thr Ala Leu Tyr Tyr Cys
    210                 215                 220 gca agg gtg cga ctt ggg gac tgg gac ttc gat gtc tgg ggc caa ggg    720
Ala Arg Val Arg Leu Gly Asp Trp Asp Phe Asp Val Trp Gly Gln Gly
225                 230                 235                 240 acc acg gtc acc gtc tcc tca                                        741
Thr Thr Val Thr Val Ser Ser
                245

<210> SEQ ID NO 6
<211> LENGTH: 247
<212> TYPE: PRT
<213> ORGANISM: Artificial Sequence
<220> FEATURE:
<223> OTHER INFORMATION: Description of Artificial Sequence: Synthetic
      scFv of Mab 679

<400> SEQUENCE: 6

Asp Ile Val Met Ser Gln Ser Pro Ser Ser Leu Ala Val Ser Pro Gly
1               5                   10                  15

Glu Lys Val Thr Met Thr Cys Lys Ser Ser Gln Ser Leu Phe Asn Ser
            20                  25                  30

Arg Thr Arg Lys Asn Tyr Leu Gly Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Asn Ser Val Gln Ser Glu Asp Leu Ala Gly Gly Ser Gly Gly Gly
                85                  90                  95

Gly Ser Glu Val Gln Leu Gln Glu Ser Gly Gly Asp Leu Val Lys Pro
            100                 105                 110

Gly Gly Ser Leu Lys Leu Ser Cys Ala Ala Ser Gly Phe Thr Phe Ser
        115                 120                 125

Ile Tyr Thr Met Ser Trp Leu Arg Gln Thr Pro Glu Lys Arg Leu Glu
    130                 135                 140

Trp Val Ala Thr Leu Ser Val Tyr Tyr Cys Thr Gln Val Tyr Tyr Leu
145                 150                 155                 160

Cys Thr Phe Gly Ala Gly Thr Lys Leu Glu Leu Lys Arg Gly Gly Gly
                165                 170                 175

Gly Ser Gly Gly Gly Asp Gly Asp Asp Ile Tyr Tyr Pro Asp Ser Val
```

-continued

```
                    180                 185                 190
Lys Gly Arg Phe Thr Ile Ser Arg Asp Asn Ala Lys Asn Asn Leu Tyr
            195                 200                 205

Leu Gln Met Asn Ser Leu Arg Ser Ala Asp Thr Ala Leu Tyr Tyr Cys
        210                 215                 220

Ala Arg Val Arg Leu Gly Asp Trp Asp Phe Asp Val Trp Gly Gln Gly
225                 230                 235                 240

Thr Thr Val Thr Val Ser Ser
                245

<210> SEQ ID NO 7
<211> LENGTH: 336
<212> TYPE: DNA
<213> ORGANISM: Artificial Sequence
<220> FEATURE:
<221> NAME/KEY: CDS
<222> LOCATION: (1)..(336)
<220> FEATURE:
<223> OTHER INFORMATION: Description of Artificial Sequence: Synthetic
      Mu-9V nucleotide sequence

<400> SEQUENCE: 7 gct gtt ttg atg acc caa act cca ctc tcc ctg cct gtc agt ctt gga      48
Ala Val Leu Met Thr Gln Thr Pro Leu Ser Leu Pro Val Ser Leu Gly
  1               5                  10                  15 gat caa gcc tcc atc tct tgc aga tct agt cag agc att gtc cat agt      96
Asp Gln Ala Ser Ile Ser Cys Arg Ser Ser Gln Ser Ile Val His Ser
                 20                  25                  30 aat ggc aac acc tat tta gaa tgg tac ctg cag aaa cca ggc cag tct     144
Asn Gly Asn Thr Tyr Leu Glu Trp Tyr Leu Gln Lys Pro Gly Gln Ser
             35                  40                  45 cca aag ctc ctg atc tac aaa gtt tcc aac cga ttt tct ggg gtc cca     192
Pro Lys Leu Leu Ile Tyr Lys Val Ser Asn Arg Phe Ser Gly Val Pro
         50                  55                  60 gac agg ttc agt ggc act gga tca ggg aca gat ttc aca gtc agg atc     240
Asp Arg Phe Ser Gly Thr Gly Ser Gly Thr Asp Phe Thr Val Arg Ile
 65                  70                  75                  80 agc aga gtg gag gct gag gat ctg gga ctt tat tac tgc ttt caa ggt     288
Ser Arg Val Glu Ala Glu Asp Leu Gly Leu Tyr Tyr Cys Phe Gln Gly
                 85                  90                  95 tca cgt gtt ccg tac acg ttc gga ggg ggg acc aag ctg gaa ata aaa     336
Ser Arg Val Pro Tyr Thr Phe Gly Gly Gly Thr Lys Leu Glu Ile Lys
            100                 105                 110

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic
      Mu-9V amino acid sequence

<400> SEQUENCE: 8

Ala Val Leu Met Thr Gln Thr Pro Leu Ser Leu Pro Val Ser Leu Gly
  1               5                  10                  15

Asp Gln Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
         50                  55                  60
```

```
Asp Arg Phe Ser Gly Thr Gly Ser Gly Thr Asp Phe Thr Val Arg Ile
 65                  70                  75                  80

Ser Arg Val Glu Ala Glu Asp Leu Gly Leu Tyr Tyr Cys Phe Gln Gly
                 85                  90                  95

Ser Arg Val Pro Tyr Thr Phe Gly Gly Gly Thr Lys Leu Glu Ile Lys
            100                 105                 110
```

<210> SEQ ID NO 9
<211> LENGTH: 333
<212> TYPE: DNA
<213> ORGANISM: Artificial Sequence
<220> FEATURE:
<221> NAME/KEY: CDS
<222> LOCATION: (1)..(333)
<220> FEATURE:
<223> OTHER INFORMATION: Description of Artificial Sequence: Synthetic
      Mu-9Vh nucleotide sequence

<400> SEQUENCE: 9

```
gtg cag ctg cag gag tca gga cct gag ctg gtg aag cct ggg gct tca      48
Val Gln Leu Gln Glu Ser Gly Pro Glu Leu Val Lys Pro Gly Ala Ser
 1               5                  10                  15 gtg aag atg tcc tgc agg gct tct gga tac acc ttc act gag tat gtt      96
Val Lys Met Ser Cys Arg Ala Ser Gly Tyr Thr Phe Thr Glu Tyr Val
             20                  25                  30 att acc tgg gta aaa cag aga act gga cag ggc ctt gag tgg att gga     144
Ile Thr Trp Val Lys Gln Arg Thr Gly Gln Gly Leu Glu Trp Ile Gly
         35                  40                  45 gag att tat cct gga agt ggt agt act tcc tac aat gaa aag ttc aag     192
Glu Ile Tyr Pro Gly Ser Gly Ser Thr Ser Tyr Asn Glu Lys Phe Lys
     50                  55                  60 ggc aag gcc aca ctg act gca gac aaa tcc tcc aac aca gcc tac atg     240
Gly Lys Ala Thr Leu Thr Ala Asp Lys Ser Ser Asn Thr Ala Tyr Met
 65                  70                  75                  80 cac ctc agc agc ctg aca tct gag gac tct gcg gtc tat ttc tgt aca     288
His Leu Ser Ser Leu Thr Ser Glu Asp Ser Ala Val Tyr Phe Cys Thr
                 85                  90                  95 aga gag gat ctt ggg ggc caa ggg act ctg gtc act gtc tct tca         333
Arg Glu Asp Leu Gly Gly Gln Gly Thr Leu Val Thr Val Ser Ser
            100                 105                 110
```

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      Mu-9Vh amino acid sequence

<400> SEQUENCE: 10

```
Val Gln Leu Gln Glu Ser Gly Pro Glu Leu Val Lys Pro Gly Ala Ser
 1               5                  10                  15

Val Lys Met Ser Cys Arg Ala Ser Gly Tyr Thr Phe Thr Glu Tyr Val
             20                  25                  30

Ile Thr Trp Val Lys Gln Arg Thr Gly Gln Gly Leu Glu Trp Ile Gly
         35                  40                  45

Glu Ile Tyr Pro Gly Ser Gly Ser Thr Ser Tyr Asn Glu Lys Phe Lys
     50                  55                  60

Gly Lys Ala Thr Leu Thr Ala Asp Lys Ser Ser Asn Thr Ala Tyr Met
 65                  70                  75                  80

His Leu Ser Ser Leu Thr Ser Glu Asp Ser Ala Val Tyr Phe Cys Thr
                 85                  90                  95
```

Arg Glu Asp Leu Gly Gly Gln Gly Thr Leu Val Thr Val Ser Ser
            100                 105                 110

<210> SEQ ID NO 11
<211> LENGTH: 333
<212> TYPE: DNA
<213> ORGANISM: Artificial Sequence
<220> FEATURE:
<221> NAME/KEY: CDS
<222> LOCATION: (1)..(333)
<220> FEATURE:
<223> OTHER INFORMATION: Description of Artificial Sequence: Synthetic humanized Mu-9 nucleotide sequence

<400> SEQUENCE: 11

```
gat atc cag ctg acc caa tcc cca ggc acc ctg tcc ctc agt cct gga       48
Asp Ile Gln Leu Thr Gln Ser Pro Gly Thr Leu Ser Leu Ser Pro Gly
 1               5                  10                  15 gag cga gcc act ctg tct tgc agg tct agt cag agc att gtg cat agt       96
Glu Arg Ala Thr Leu Ser Cys Arg Ser Ser Gln Ser Ile Val His Ser
                20                  25                  30 aat ggc aac acc tat tta gaa tgg tac ctg cag aaa cca ggc cag gct      144
Asn Gly Asn Thr Tyr Leu Glu Trp Tyr Leu Gln Lys Pro Gly Gln Ala
            35                  40                  45 cca agg ctc ctg atc tac aaa gtt tcc aac cga ttt tcc gga gtc cca      192
Pro Arg Leu Leu Ile Tyr Lys Val Ser Asn Arg Phe Ser Gly Val Pro
        50                  55                  60 gac agg ttc agt ggc tct gga tca ggg aca gat ttc aca ctt act atc      240
Asp Arg Phe Ser Gly Ser Gly Ser Gly Thr Asp Phe Thr Leu Thr Ile
 65                 70                  75                  80 agc aga ctg gag cct gag gat ttt gct gtg tat tac tgc ttt caa ggt      288
Ser Arg Leu Glu Pro Glu Asp Phe Ala Val Tyr Tyr Cys Phe Gln Gly
                85                  90                  95 tca cgt gtt ccg tac acg ttc gga ggg ggg acc aag gtg gag atc          333
Ser Arg Val Pro Tyr Thr Phe Gly Gly Gly Thr Lys Val Glu Ile
            100                 105                 110
```

<210> SEQ ID NO 12
<211> LENGTH: 111
<212> TYPE: PRT
<213> ORGANISM: Artificial Sequence
<220> FEATURE:
<223> OTHER INFORMATION: Description of Artificial Sequence: Synthetic humanized Mu-9 amino acid sequence

<400> SEQUENCE: 12

Asp Ile Gln Leu Thr Gln Ser Pro Gly Thr Leu Ser Leu Ser Pro Gly
 1               5                  10                  15

Glu Arg Ala Thr Leu Ser Cys Arg Ser Ser Gln Ser Ile Val His Ser
                20                  25                  30

Asn Gly Asn Thr Tyr Leu Glu Trp Tyr Leu Gln Lys Pro Gly Gln Ala
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Thr Ile
 65                 70                  75                  80

Ser Arg Leu Glu Pro Glu Asp Phe Ala Val Tyr Tyr Cys Phe Gln Gly
                85                  90                  95

Ser Arg Val Pro Tyr Thr Phe Gly Gly Gly Thr Lys Val Glu Ile
            100                 105                 110

```
<210> SEQ ID NO 13
<211> LENGTH: 333
<212> TYPE: DNA
<213> ORGANISM: Artificial Sequence
<220> FEATURE:
<221> NAME/KEY: CDS
<222> LOCATION: (1)..(333)
<220> FEATURE:
<223> OTHER INFORMATION: Description of Artificial Sequence: Synthetic
      humanized Mu-9 heavy chain variable region nucleotide sequence

<400> SEQUENCE: 13 gtg cag ctg cag cag tca gga gct gag gtg aaa aag cct ggg agc tca      48
Val Gln Leu Gln Gln Ser Gly Ala Glu Val Lys Lys Pro Gly Ser Ser
 1               5                  10                  15 gtg aag gtc tcc tgc aag gct tct gga tac acc ttc act gag tat gtt      96
Val Lys Val Ser Cys Lys Ala Ser Gly Tyr Thr Phe Thr Glu Tyr Val
             20                  25                  30 att acc tgg gta aaa cag aga cct gga cag ggt cta gag tgg att gga    144
Ile Thr Trp Val Lys Gln Arg Pro Gly Gln Gly Leu Glu Trp Ile Gly
         35                  40                  45 gag att tat cct gga agt ggt agt act tcc tac aat gaa aag ttc aag    192
Glu Ile Tyr Pro Gly Ser Gly Ser Thr Ser Tyr Asn Glu Lys Phe Lys
 50                  55                  60 ggc aag gcc aca atc act gct gac aaa tcc act aac aca gcc tac atg    240
Gly Lys Ala Thr Ile Thr Ala Asp Lys Ser Thr Asn Thr Ala Tyr Met
65                  70                  75                  80 gag ctc agc agc ctg aga tct gag gac act gcg ttc tat ttc tgt aca    288
Glu Leu Ser Ser Leu Arg Ser Glu Asp Thr Ala Phe Tyr Phe Cys Thr
                 85                  90                  95 aga gag gat ctt ggg ggc caa ggg tct ctg gtc acc gtc tct tca         333
Arg Glu Asp Leu Gly Gly Gln Gly Ser Leu Val Thr Val Ser Ser
            100                 105                 110

<210> SEQ ID NO 14
<211> LENGTH: 111
<212> TYPE: PRT
<213> ORGANISM: Artificial Sequence
<220> FEATURE:
<223> OTHER INFORMATION: Description of Artificial Sequence: Synthetic
      humanized Mu-9 heavy chain variable region amino acid sequence

<400> SEQUENCE: 14

Val Gln Leu Gln Gln Ser Gly Ala Glu Val Lys Lys Pro Gly Ser Ser
 1               5                  10                  15

Val Lys Val Ser Cys Lys Ala Ser Gly Tyr Thr Phe Thr Glu Tyr Val
             20                  25                  30

Ile Thr Trp Val Lys Gln Arg Pro Gly Gln Gly Leu Glu Trp Ile Gly
         35                  40                  45

Glu Ile Tyr Pro Gly Ser Gly Ser Thr Ser Tyr Asn Glu Lys Phe Lys
 50                  55                  60

Gly Lys Ala Thr Ile Thr Ala Asp Lys Ser Thr Asn Thr Ala Tyr Met
65                  70                  75                  80

Glu Leu Ser Ser Leu Arg Ser Glu Asp Thr Ala Phe Tyr Phe Cys Thr
                 85                  90                  95

Arg Glu Asp Leu Gly Gly Gln Gly Ser Leu Val Thr Val Ser Ser
            100                 105                 110

<210> SEQ ID NO 15
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(HSG)
<220> FEATURE:
<221> NAME/KEY: MOD_RES
<222> LOCATION: (4)
<223> OTHER INFORMATION: Lys(HSG)
<220> FEATURE:
<223> OTHER INFORMATION: c-term amidated

<400> SEQUENCE: 15

Phe Lys Tyr Lys
  1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Lys(DTPA)
<220> FEATURE:
<221> NAME/KEY: MOD_RES
<222> LOCATION: (3)
<223> OTHER INFORMATION: Lys(DTPA)
<220> FEATURE:
<221> NAME/KEY: MOD_RES
<222> LOCATION: (4)
<223> OTHER INFORMATION: Lys(Tscg-Cys); Cys not part of peptide backbone
<220> FEATURE:
<223> OTHER INFORMATION: c-term amidated

<400> SEQUENCE: 16

Lys Tyr Lys Lys
  1

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: GlySer
      linker peptide

<400> SEQUENCE: 17

Gly Gly Gly Gly Ser Gly Gly Gly Gly Ser Gly Gly Gly Gly Ser
  1               5                  10                  15

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Lys Tyr Lys
  1
```